US012595220B2

(12) United States Patent
Bofill Herrera et al.

(10) Patent No.: US 12,595,220 B2
(45) Date of Patent: Apr. 7, 2026

(54) COCRYSTALS OF PTEROSTILBENE AND COMPOSITIONS COMPRISING THEM

(71) Applicant: CENTER FOR INTELLIGENT RESEARCH IN CRYSTAL ENGINEERING, S.L., Palma de Mallorca (ES)

(72) Inventors: Lidia Bofill Herrera, Bigues I Riells (ES); Dafne De Sande López, L'Hospitalet de Llobregat (ES); Rafel Prohens López, Sabadell (ES); Rafael Barbas Cañero, Santa Coloma de Gramenet (ES)

(73) Assignee: CENTER FOR INTELLIGENT RESEARCH IN CRYSTAL ENGINEERING, S.L., Palma de Mallorca (ES)

( * ) Notice: Subject to any disclaimer, the term of this patent is extended or adjusted under 35 U.S.C. 154(b) by 775 days.

(21) Appl. No.: 17/786,510

(22) PCT Filed: Dec. 18, 2020

(86) PCT No.: PCT/EP2020/087017

§ 371 (c)(1),
(2) Date: Jun. 16, 2022

(87) PCT Pub. No.: WO2021/123162

PCT Pub. Date: Jun. 24, 2021

(65) Prior Publication Data

US 2023/0048512 A1 Feb. 16, 2023

(30) Foreign Application Priority Data

Dec. 20, 2019 (EP) .................................... 19383178
Mar. 9, 2020 (EP) .................................... 20382170

(51) Int. Cl.

| | |
|---|---|
| ***C07D 213/55*** | (2006.01) |
| ***C07C 43/23*** | (2006.01) |
| *A23K 20/10* | (2016.01) |
| *A23L 33/10* | (2016.01) |
| *A61K 8/33* | (2006.01) |
| *A61K 31/085* | (2006.01) |
| *A61P 3/02* | (2006.01) |
| *A61P 39/06* | (2006.01) |
| *A61Q 19/00* | (2006.01) |
| *C07C 65/05* | (2006.01) |
| *C07C 211/10* | (2006.01) |
| *C07C 229/26* | (2006.01) |
| *C07C 275/02* | (2006.01) |
| *C07D 209/04* | (2006.01) |
| *C07D 213/79* | (2006.01) |
| *C07D 239/557* | (2006.01) |
| *C07D 241/04* | (2006.01) |
| *C07D 257/02* | (2006.01) |
| *C07D 295/03* | (2006.01) |
| *C07D 471/04* | (2006.01) |
| *C07D 473/08* | (2006.01) |
| *C07D 487/04* | (2006.01) |
| *C07D 487/08* | (2006.01) |
| *C07D 487/10* | (2006.01) |

(52) U.S. Cl.
CPC ............ *C07C 43/23* (2013.01); *C07D 213/55* (2013.01); *C07B 2200/13* (2013.01)

(58) Field of Classification Search
CPC ....... C07C 43/23; C07C 65/05; C07D 213/55; C07D 241/04; C07D 213/79; C07D 257/02; C07B 2200/13
See application file for complete search history.

(56) References Cited

U.S. PATENT DOCUMENTS 8,318,807 B2 * 11/2012 Schultheiss ............. C07C 43/23 568/646
2011/0144053 A1 6/2011 Bhaskaran et al.

FOREIGN PATENT DOCUMENTS

WO WO 2011/097372 A2 8/2011
WO WO 2013/144916 A1 10/2013
WO WO 2019/153088 A1 8/2019

OTHER PUBLICATIONS

Estrela JM, Ortega A, Mena S, Rodriguez ML, Asensi M. Pterostilbene: Biomedical applications. Crit Rev Clin Lab Sci. May-Jun. 2013;50(3):65-78. doi: 10.3109/10408363.2013.805182. Epub Jul. 1, 2013. PMID: 23808710. (Year: 2013).*
International Search Report and Written Opinion mailed May 4, 2021 for International Application No. PCT/EP2020/087017, 24 pages.
Banik et al: "Cocrystal and Salt Forms of Furosemide: Solubility and Diffusion Variations", Crystal Growth & Design; Aug. 3, 2016; vol. 16(9), pp. 5418-5428; DOI:10.1021/acs.cgd.6b00902; ISSN 1528-7483.
Gravestock et al: "The "GI dissolution" method: a low volume, in vitro apparatus for assessing the dissolution/precipitation behaviour of an active pharmaceutical ingredient under biorelevant conditions", Analytical Methods 2011, vol. 3, pp. 560-567.
Yamashita et al: "Coformer Screening Using Thermal Analysis Based on Binary Phase Diagrams", Pharmaceutical Research; Dec. 13, 2014; vol. 31(8), pp. 1946-1957; DOI:10.1007/S11095-014-1296-4.

* cited by examiner

*Primary Examiner* — Bruck Kifle
*Assistant Examiner* — Kevin S Martin
(74) *Attorney, Agent, or Firm* — SQUIRE PATTON BOGGS (US)

(57) ABSTRACT

The present disclosure relates to a cocrystal of pterostilbene and a coformer capable to form hydrogen bond interactions, to a process for the preparation thereof, and to its use as a medicament or a dietary supplement. The present disclosure also relates to a composition comprising the cocrystal.

10 Claims, 12 Drawing Sheets

COCRYSTALS OF PTEROSTILBENE AND COMPOSITIONS COMPRISING THEM

CROSS-REFERENCE

The present application is a national-phase filing under 35 U.S.C. § 371 of International Application No. PCT/EP2020/087017 (filed Dec. 18, 2020), which claims the benefit of European Patent Application Nos. 19383178.1 (filed Dec. 20, 2019) and 20382170.7 (filed Mar. 9, 2020), all of which applications are incorporated herein by reference in their entirety.

TECHNICAL FIELD

The present disclosure relates to cocrystals of pterostilbene, to processes for the preparation thereof, and to their use as a medicament or a dietary supplement. It also relates to compositions comprising them.

BACKGROUND ART

Pterostilbene (trans-3,5-dimethoxy-4-hydroxystilbene) is a natural dietary compound and the primary antioxidant component of blueberries. It has increased bioavailability in comparison to other stilbene compounds, which may enhance its dietary benefit and possibly contribute to a valuable clinical effect.

The structure of pterostilbene corresponds to the formula (I):

(I)

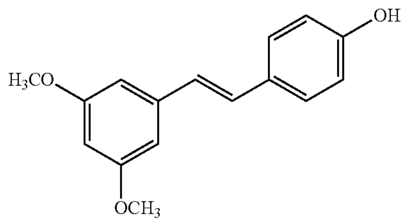

Multiple studies have demonstrated the antioxidant activity of pterostilbene and its clinical potential in the prevention and treatment of various medical conditions including neurological, cardiovascular, metabolic, and hematologic disorders. Particularly, the antioxidant activity of pterostilbene has been related with anticarcinogenesis, modulation of neurological disease, anti-inflammation, attenuation of vascular disease, amelioration of diabetes and of other age-related diseases.

Pterostilbene is supplied as a crystalline solid having a melting point of 89-92° C. It is sparingly soluble in water.

A basic requirement for satisfactory bioavailability is that the active ingredient is able to dissolve adequately in the digestive tract. The low water solubility of pterostilbene poses some problems regarding to its bioavailability.

It is known that different solid forms of a active ingredient can have different characteristics, and offer certain advantages, for example with regard to solubility or bioavailability. Thus, the discovery of new solid forms allows for improving the pharmacokinetic properties of the active ingredients and as a consequence the characteristics of the pharmaceutical formulations containing the active ingredients, since some forms are more adequate for one type of formulation, and other forms for other different formulations.

Particularly, in recent years cocrystal formation has emerged as a viable strategy towards improving the pharmacokinetic data of active ingredients. By cocrystallizing an active ingredient or a salt of an active ingredient with a coformer (the second component of the cocrystal), a new solid state form of the active ingredient is created having unique properties compared with existing solid forms of the active ingredient or its salts. Such different properties may provide a basis for improving formulation, for example, by facilitating better processing or handling characteristics, changing the dissolution profile in a favourable direction, or improving stability and shelf-life. However, cocrystal formation is not predictable, and in fact is not always possible. Moreover, there is no way to predict the properties of a particular cocrystal of a compound until it is formed. Finding the appropriate coformers and right conditions to obtain a particular cocrystal can take significant time, effort and resources.

From what is known in the art, there is still the need of finding new more soluble solid forms of pterostilbene in order to improve the pharmaceutical properties of the pharmaceutical formulations containing them, particularly in terms of bioavailability.

SUMMARY OF INVENTION

The inventors have found that pterostilbene can form a cocrystal with a coformer capable to form hydrogen bond interactions as defined herein below. The provision of the mentioned cocrystals of pterostilbene gives a new tool to overcome the problems associated with the water solubility of pterostilbene because it has been found that these cocrystals have a better water solubility and higher dissolution rate in aqueous media, what makes them more bioavailable. This property makes the cocrystals more suitable for preparing pharmaceutical or dietary compositions containing pterostilbene.

Cocrystal formation, particularly with a coformer capable to form hydrogen bond interactions, cannot be predicted.

Accordingly, the provision of an improved-crystal form of pterostilbene in the form of a cocrystal with a coformer capable to form hydrogen bond interactions as defined herein below is considered a contribution to the art.

Thus, a first aspect of the present disclosure refers to the provision of a cocrystal of pterostilbene and a coformer capable to form hydrogen bond interactions.

A second aspect of the present disclosure refers to a composition comprising an effective amount of the cocrystal of pterostilbene and a coformer capable to form hydrogen bond interactions as defined herein above and below together, with one or more appropriate acceptable excipients or carriers.

Finally, a third aspect of the present disclosure refers to a cocrystal of pterostilbene and a coformer capable to form hydrogen bond interactions as defined herein above and below for use as a medicament.

○ Pterostilbene Form I
♦ Pterostilbene:picolinic acid cocrystal (1:1)
● Pterostilbene:ethylendiamine hydrate cocrystal
⊠ Pterostilbene:2,3,5-trimethylpirazine cocrystal
◇ Pterostilbene Form VI
▲ Pterostilbene:ethylendiamine cocrystal
:: Pterostilbene:theophylline DCM solvate cocrystal
■ Pterostilbene:caffeine cocrystal.

Figure 17:
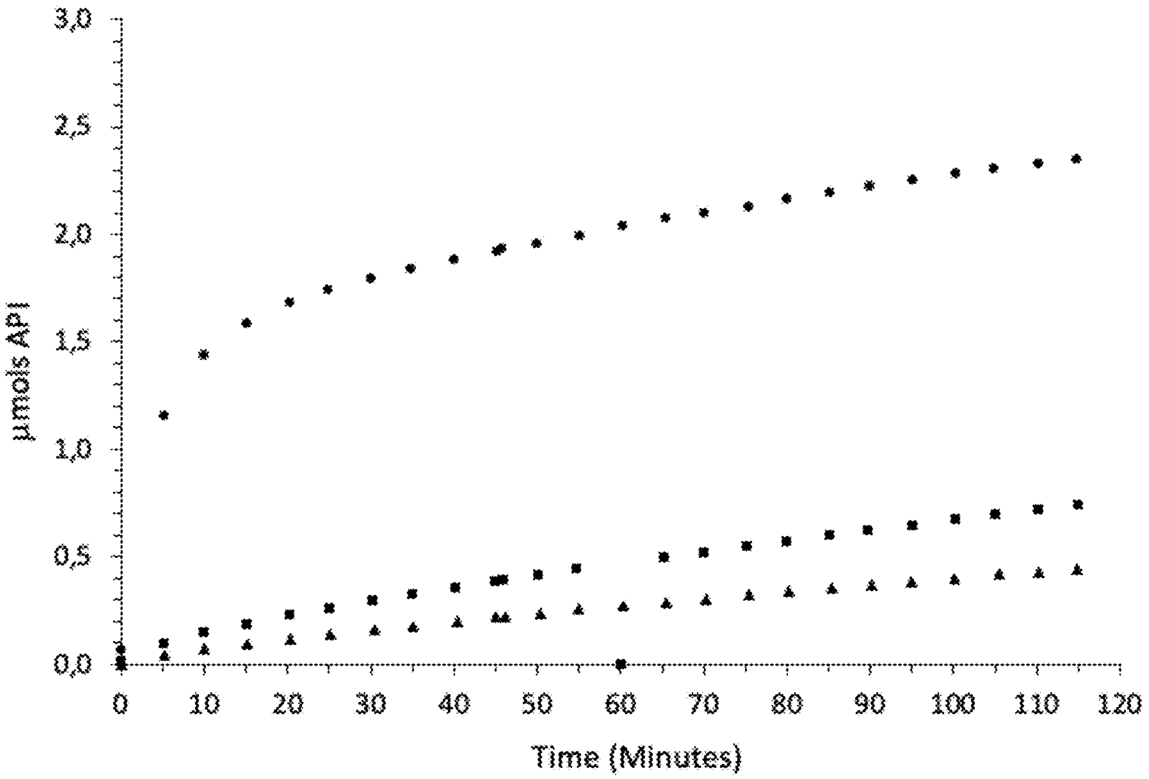

FIG. 17 shows the dissolution profile of pterostilbene: picolinic acid cocrystal 2:1, compared to perostilbene Form I and pterostilbene Form VI, where:

● Pterostilbene:picolinic acid cocrystal 2:1
■ Pterostilbene Form I
▲ A Pterostilbene Form VI.

Figure 18:
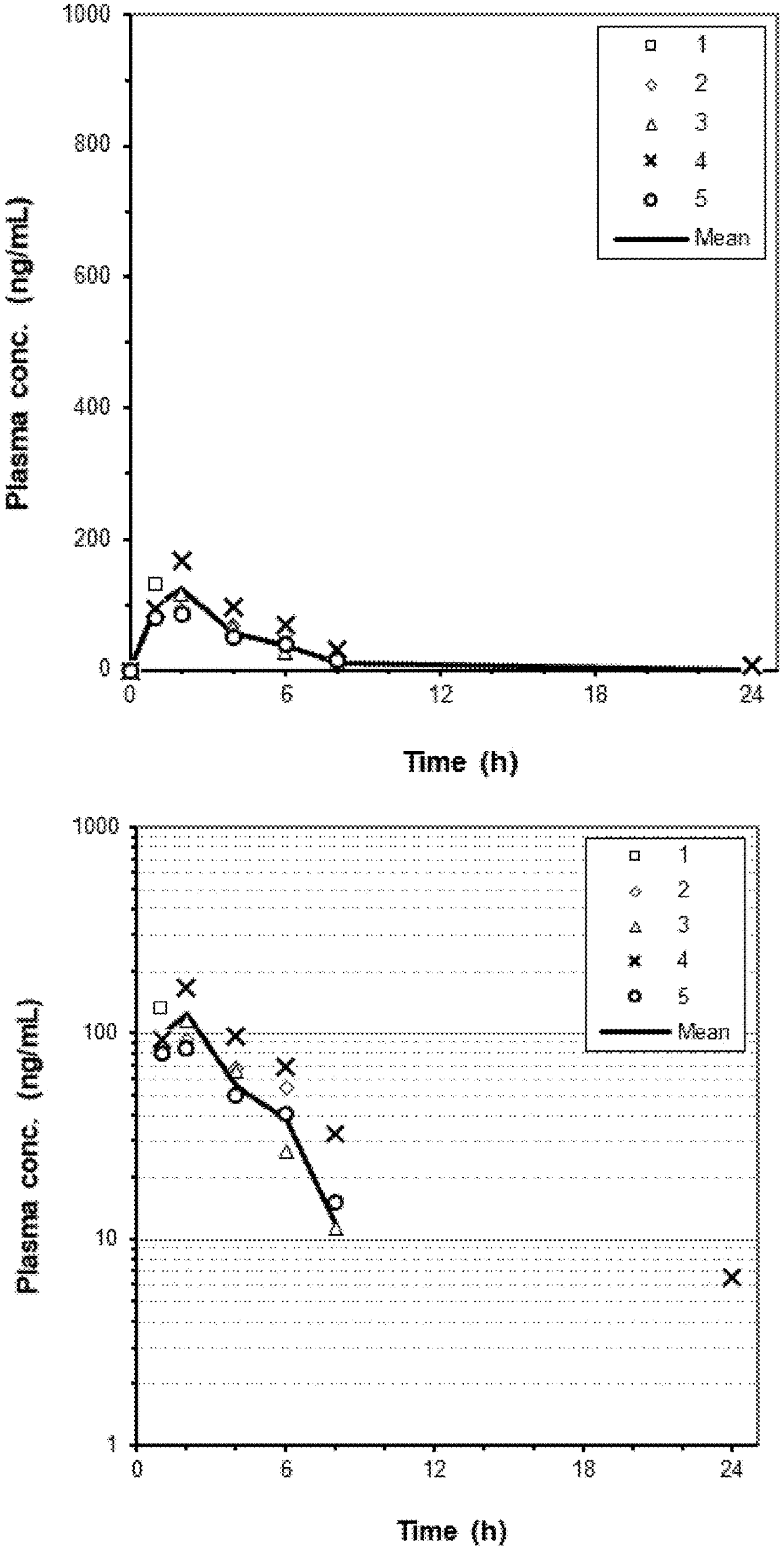

FIG. 18 shows the plasma concentration-time profile of pterostilbene in rats after single oral administration (20 mg/kg pterostilbene, free base).

Figure 19:
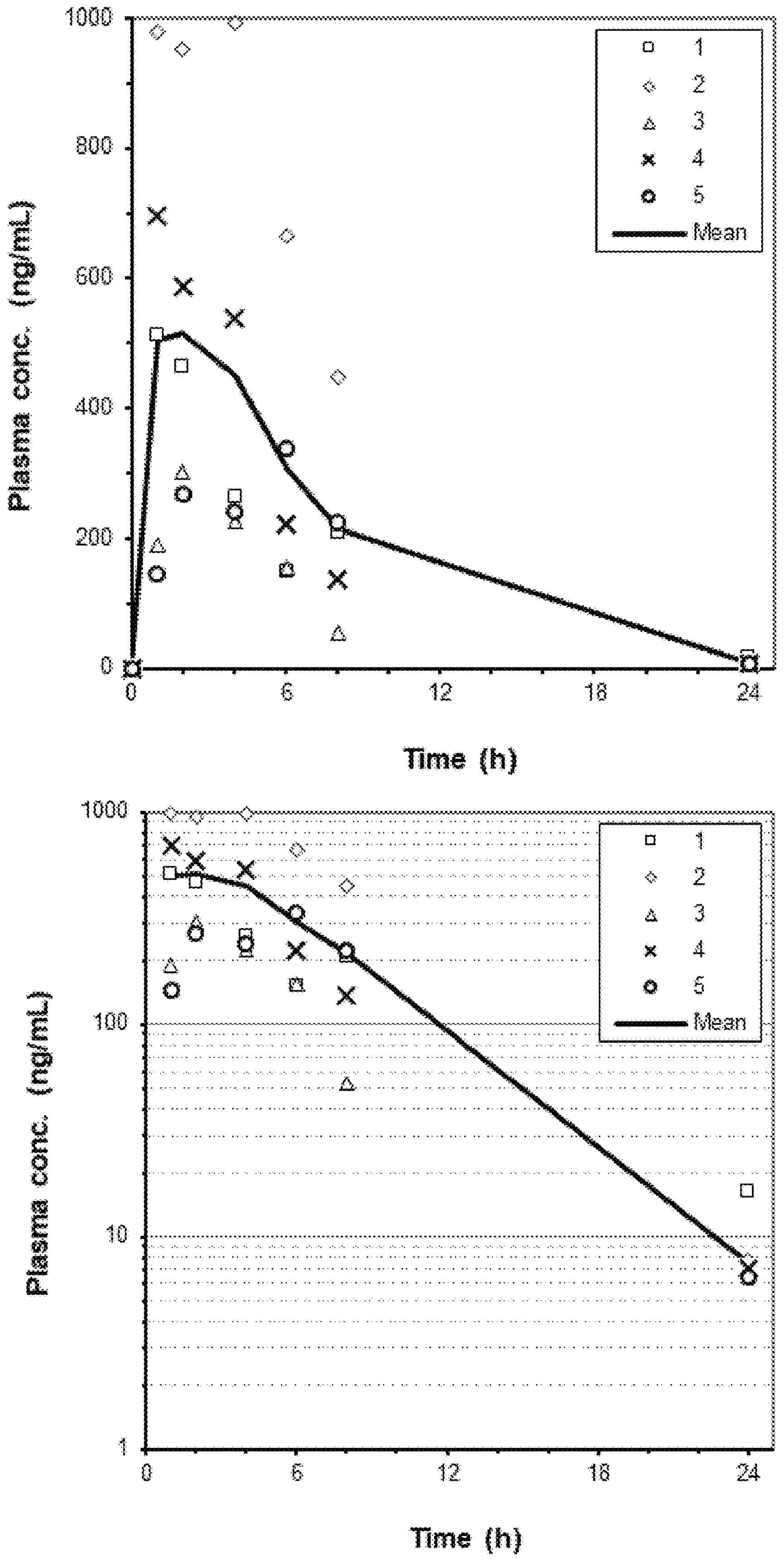

FIG. 19 shows the plasma concentration-time profile of pterostilbene in rats after single oral administration of cocrystal of pterostilbene and picolinic acid (20 mg/kg P56-VIII; 13.5 mg as pterostilbene).

Figure 20:
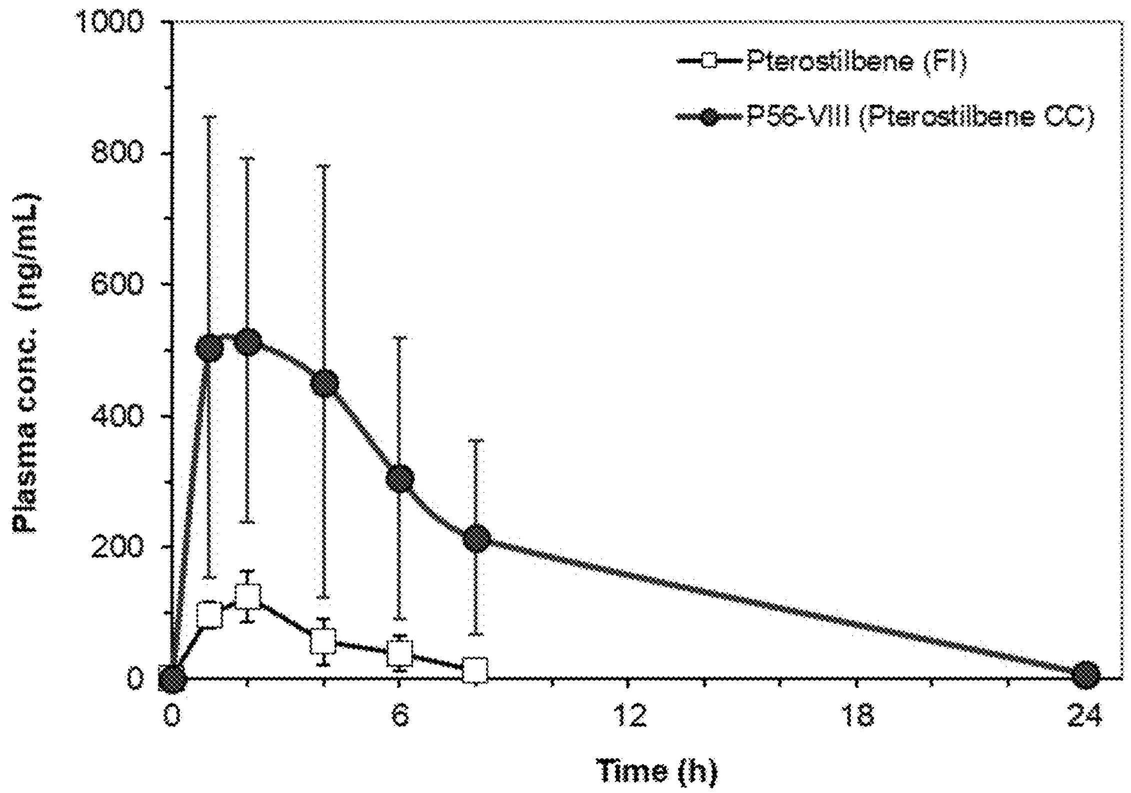

FIG. 20 shows the comparison of plasma concentration-time profiles of pterostilbene in male SD rats after single oral administration of perostilbene free base (20 mg/kg P56) and cocrystal of pterostilbene and picolinic acid (20 mg/kg P56-VIII, 13.5 mg/kg pterostilbene). Arithmetic mean values ±SD.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For the purposes of the present-disclosure, ranges given, such as of temperatures, times, and the like, should be considered approximate, unless specifically stated.

For the purposes of the present disclosure, the term "cocrystal" refers herein to a crystalline entity with at least two different components constituting the unit cell at room temperature (20-25° C.) and interacting by intermolecular interactions. Thus, in a cocrystal, one component crystallizes together with one or more neutral components.

The cocrystals may include one or more solvent molecules in the crystal lattice. Thus, the term "cocrystal hydrate" or "hydrate cocrystal" have the same meaning and are used interchangeable. They refer to a cocrystal including water as a solvent in the crystal lattice. Similarly, cocrystals including other solvents such as dichloromethane can be formed.

The expression "cocrystal obtainable by" is used here to define each specific cocrystal of the present disclosure by the process for obtaining it and refers to the product obtainable by any of the corresponding processes disclosed herein. For the purposes of the present disclosure the expressions "obtainable", "obtained" and equivalent expressions are used interchangeably and, in any case, the expression "obtainable" encompasses the expression "obtained".

The term "coformer capable to form hydrogen bond interactions" refers to a compound having hydrogen atoms bound to an electronegative atom (such as nitrogen, oxygen, or sulfur) or a compound having basic atoms (such as nitrogen or oxygen) and with the ability to stablish strong intermolecular hydrogen-bonds. Examples of coformer capable to form hydrogen bond interactions include phosphoric acids, carboxylic acids, alcohols, imidazols, thioamides, sulfinamides, pyrroles, ureas, amides, sulfonamides, carbamates, amines, ketones and sulphoxides.

When values of characteristic peaks of an X-ray diffractogram are given it is said that these are "approximate" values. It should be understood that the values are the ones shown in the corresponding lists or tables ±0.3 degrees 2 theta measured in an X-ray diffractometer with Cu-$K_\alpha$ radiation $\lambda$=1.5418 Å.

When a ratio of components of the cocrystals of the present disclosure is specified it refers to the molar ratio of the components that forms the cocrystal. The term "molar ratio" has been used to express the stoichiometric amount in moles of each of the components of a cocrystal. The molar ratio can be determined by $^1$H NMR (Proton nuclear magnetic resonance), thermogravimetric analysis (TGA) or single crystal X-ray diffraction (SCXRD).

When values of molar ratio are given according to TGA or $^1$H NMR it is said that these are "approximate" values due to the measurement error. It should be understood that when a molar ratio is mentioned, it corresponds to a molar ratio ±0.2%. The variability of the results is due to the inherent sensibility of the TGA or $^1$H NMR equipment.

The term "room temperature" refers to a temperature of the environment, without heating or cooling, and is generally from 20° C. to 25° C.

The term "overnight" refers to a time interval of from 10 h to 20 h.

As used herein, the indefinite articles "a" and "an" are synonymous with "at least one" or "one or more". Unless indicated otherwise, definite articles used herein, such as "the", also include the plural of the noun.

As mentioned above, the first aspect of the present disclosure is the provision of a cocrystal of pterostilbene and a coformer capable to form hydrogen bond interactions. Also as mentioned above, the cocrystal of the present disclosure may be in crystalline form either as free solvation compound or as a solvate (e.g. a hydrate or a dichloromethane solvate) and it is intended that both forms are within the scope of the present disclosure. Methods of solvation are generally known within the art.

Particularly, the coformer is selected from the group consisting of picolinic acid, 1,4-dimethylpiperazine, 2,3,5-trimethylpyrazine, theophylline, ethylenediamine, 1,4-diazabicyclo[2.2.2]octane (DABCO), 1,4,8,11-tetrazacyclohexandecane, 2,4-dihydroxybenzoic acid (2,4-DHBA), indole, lysine, orotic acid, phenanthroline, and urea.

In an embodiment, the coformer is a carboxylic acid, particularly a carboxylic acid selected from the group consisting of picolinic acid, 2,4-dihydroxybenzoic acid, orotic acid, indole, and lysine.

In an embodiment, the coformer is picolinic acid. In a particular embodiment, the cocrystal of pterostilbene and picolinic acid is characterized by having an X-ray powder diffractogram that comprises characteristic peaks at approximately 5.6 and 14.0±0.3 degrees 2 theta (Cu-$K_\alpha$ radiation, $\lambda$=1.5418 Å). Particularly, the cocrystal of pterostilbene and picolinic acid of the present disclosure is characterized by having an X-ray powder diffractogram that comprises further characteristic peaks at 13.5, 21.8 and 24.4±0.3 degrees 2 theta (Cu-$K_\alpha$ radiation, $\lambda$=1.5418 Å). More particularly, the molar ratio of pterostilbene to picolinic acid is 1:1.

More specifically, the cocrystal of pterostilbene and picolinic acid [1:1] of the present disclosure is characterized by exhibiting in the X-ray powder diffractogram a pattern of peaks, expressed in 2 theta units in degrees, 2θ (°), which is shown in Table 1.

TABLE 1

List of selected peaks (only peaks with relative intensity greater than or equal to 1% are indicated):

| Pos. [°2Th.] | Rel. Int. [%] |
|---|---|
| 5.6169 | 33.15 |
| 11.2739 | 12.33 |
| 12.346 | 31.99 |
| 13.4496 | 35.69 |
| 13.9625 | 89.18 |
| 15.3097 | 13.08 |
| 15.99 | 10.56 |
| 16.9149 | 17.72 |
| 18.6129 | 17.71 |
| 18.809 | 16.7 |
| 19.5284 | 22.76 |
| 19.9678 | 8.47 |
| 21.0446 | 21.91 |
| 21.6278 | 7.78 |
| 21.8238 | 63.62 |
| 22.071 | 44.8 |
| 23.5635 | 7.54 |
| 23.932 | 6.82 |
| 24.3877 | 100 |
| 24.6273 | 10.26 |
| 24.858 | 12.15 |
| 25.4181 | 25.59 |
| 26.2045 | 12.31 |
| 27.0818 | 9.5 |
| 29.353 | 24.27 |
| 29.603 | 21.9 |
| 30.8981 | 8.78 |

Figure 1:
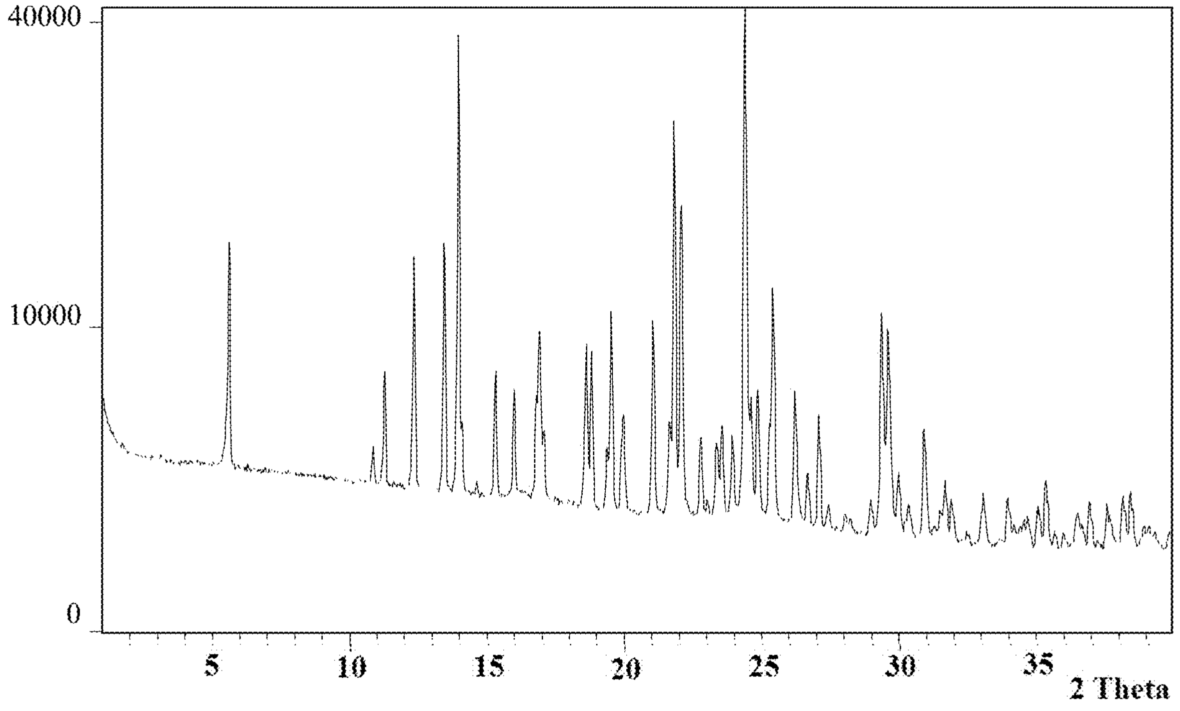
FIG. 1 shows the X-ray powder diffractogram (XRPD) of cocrystal of pterostilbene and picolinic acid (1:1).

The cocrystal of pterostilbene and picolinic acid [1:1] of the present disclosure may be further characterized by an X-ray diffractogram as in FIG. 1.

In another particular embodiment, the cocrystal of pterostilbene and picolinic acid is characterized by having an X-ray powder diffractogram that comprises characteristic peaks at approximately 18.3 and 26.0±0.3 degrees 2 theta (Cu-$K_\alpha$ radiation, $\lambda$=1.5418 Å). Particularly, the cocrystal of pterostilbene and picolinic acid of the present disclosure is characterized by having an X-ray powder diffractogram that comprises further characteristic peaks at 3.2, 16.8 and 23.6±0.3 degrees 2 theta (Cu-$K_\alpha$ radiation, $\lambda$=1.5418 Å). More particularly, the molar ratio of pterostilbene to picolinic acid is-2:1.

More specifically, the cocrystal of pterostilbene and picolinic acid [2:1] of the present disclosure is characterized by exhibiting in the X-ray powder diffractogram a pattern of peaks, expressed in 2 theta units in degrees, 2θ (°), which is shown in Table 2 (only peaks with relative intensity greater than or equal to 1% are indicated).

TABLE 2

| Pos. [°2Th.] | Rel. Int. [%] |
|---|---|
| 3.2296 | 87.84 |
| 6.4402 | 21.29 |
| 9.5395 | 22.26 |
| 9.8263 | 12.62 |
| 10.5625 | 9.23 |
| 15.8652 | 11.37 |
| 16.8271 | 38.15 |
| 17.1356 | 20.43 |
| 17.4453 | 28.77 |
| 18.3181 | 67.28 |
| 18.6681 | 12.78 |
| 19.1243 | 23.32 |
| 19.4168 | 16.33 |
| 19.6903 | 17.62 |
| 20.2394 | 6.17 |
| 22.2772 | 14.18 |
| 23.5945 | 53.51 |
| 23.8152 | 14.6 |
| 24.0743 | 51.67 |
| 25.6849 | 17.99 |
| 26.0389 | 100 |
| 26.829 | 12.3 |
| 27.8083 | 7.22 |
| 28.2253 | 10.49 |
| 28.7149 | 7.38 |
| 29.0089 | 17.16 |

Figure 2:
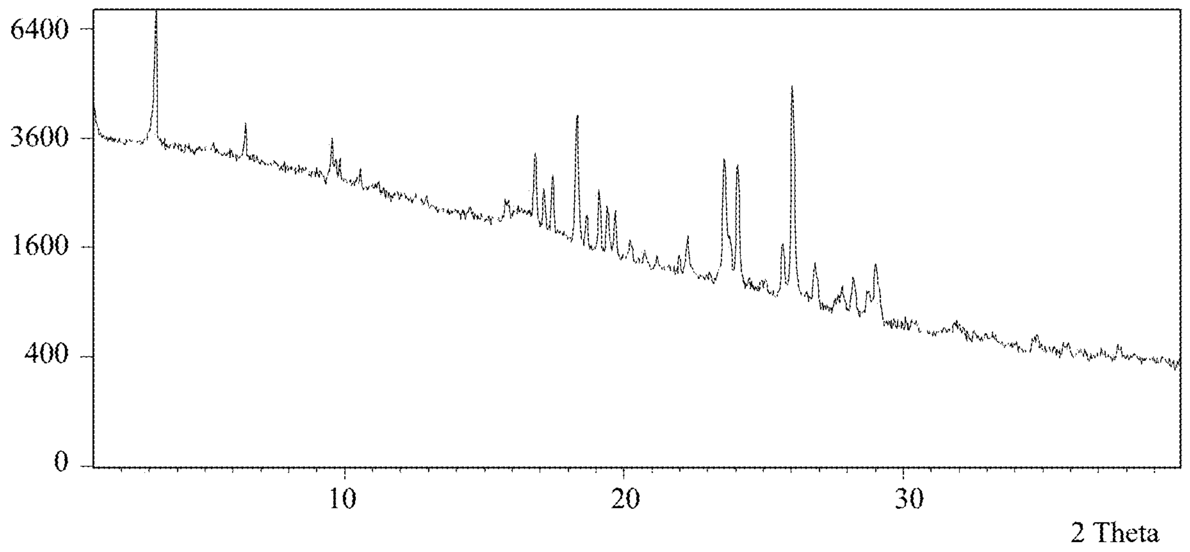
FIG. 2 shows the X-ray powder diffractogram (XRPD) of cocrystal of pterostilbene and picolinic acid (2:1).

The cocrystal of pterostilbene and picolinic acid [2:1] of the present disclosure may be further characterized by an X-ray diffractogram as in FIG. 2.

In another embodiment, the coformer is 1,4-dimethylpiperazine, and the cocrystal of pterostilbene and 1,4-dimethylpiperazine is characterized by having an X-ray powder diffractogram that comprises characteristic peaks at approximately 17.3 and 21.2±0.3 degrees 2 theta (Cu-$K_\alpha$ radiation, $\lambda$=1.5418 Å). Particularly, the cocrystal of pterostilbene and 1,4-dimethylpiperazine of the present disclosure is characterized by having an X-ray powder diffractogram that comprises further characteristic peaks at 6.9, 13.7 and 15.8±0.3 degrees 2 theta (Cu-$K_\alpha$ radiation, $\lambda$=1.5418 Å). More particularly, the molar ratio of pterostilbene to 1,4-dimethylpiperazine is 2:1.

More specifically, the cocrystal of pterostilbene and 1,4-dimethylpiperazine of the present disclosure is characterized by exhibiting in the X-ray powder diffractogram a pattern of peaks, expressed in 2 theta units in degrees, 2θ (°), which is shown in Table 2.

TABLE 3

List of selected peaks (only peaks with relative intensity greater than or equal to 1% are indicated):

| Pos. [°2Th.] | Rel. Int. [%] |
|---|---|
| 6.8894 | 26.57 |
| 10.5211 | 21.64 |
| 13.7014 | 71.72 |
| 15.751 | 48.36 |

TABLE 3-continued

| List of selected peaks (only peaks with relative intensity greater than or equal to 1% are indicated): | |
|---|---|
| Pos. [°2Th.] | Rel. Int. [%] |
| 15.9548 | 24.75 |
| 16.4869 | 5.82 |
| 16.6605 | 30.99 |
| 16.9633 | 6.88 |
| 17.3097 | 82.43 |
| 17.7078 | 16.93 |
| 18.3773 | 20.85 |
| 18.5668 | 16.6 |
| 19.0475 | 39.34 |
| 20.6378 | 7.91 |
| 21.2175 | 100 |
| 21.371 | 31.19 |
| 21.7758 | 13.97 |
| 21.9854 | 11.06 |
| 22.2378 | 21.28 |
| 25.7444 | 7.52 |
| 26.0175 | 9.4 |
| 26.4516 | 13.36 |
| 28.1315 | 30.2 |
| 28.4889 | 5.32 |
| 29.3592 | 9.47 |
| 31.9421 | 6.8 |
| 33.3093 | 5.17 |

The data of the structure of the cocrystal of pterostilbene and 1,4-dimethylpiperazine defined above obtained by single crystal X-ray diffraction correspond to a cocrystal and are shown below:

| Structure | cocrystal pterostilbene: 1,4-dimethylpiperazine |
|---|---|
| Temperature (K) | 100(2) |
| Wavelength (Å) | 0.71073 |
| Crystal system | Monoclinic |
| space group | $P2_1/c$ |
| a, b, c (Å) | 10.4766(4), 6.6402(3), 25.5452(12) |
| α, β, γ (°) | 90, 93.391(2), 90 |
| Volume ($Å^3$) | 1773.98(13) |
| Z, Density (calc.) ($Mg/m^3$) | 4, 1.173 |
| Final R indices [l > 2σ(l)] | R1 = 0.0475, wR2 = 0.1318 |

Figure 3:
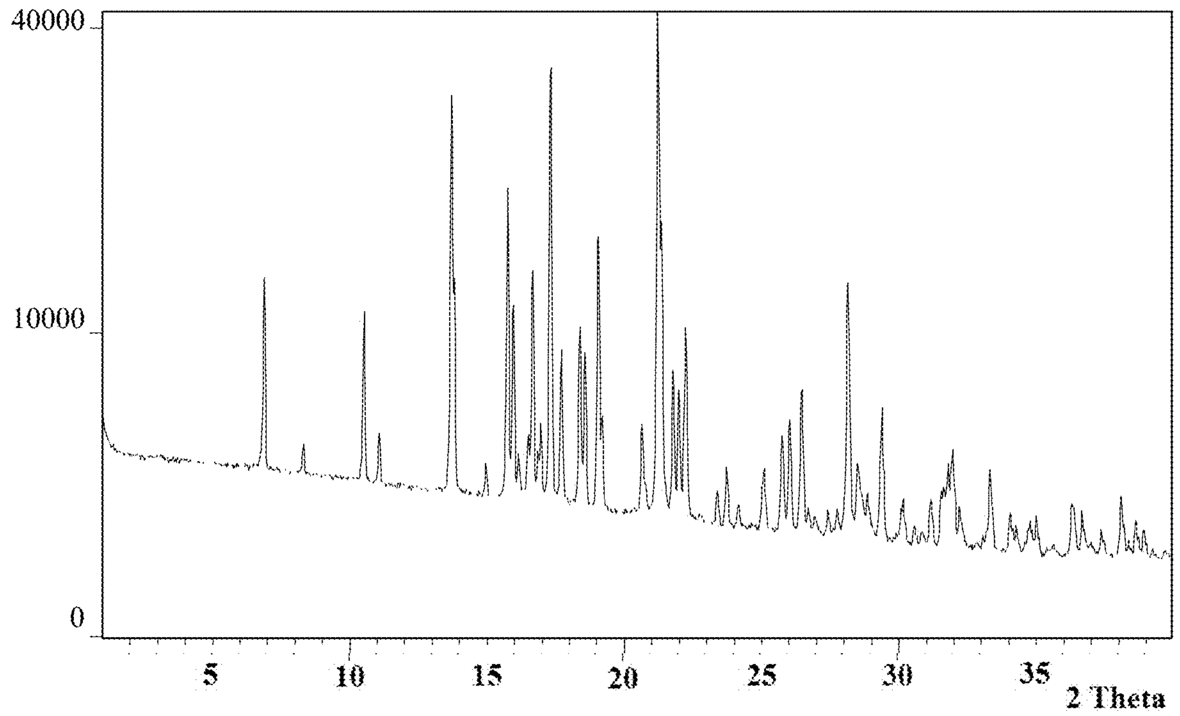
FIG. 3 shows the XRPD of cocrystal of pterostilbene and 1,4-dimethylpiperazine (2:1).

The cocrystal of pterostilbene and 1,4-dimethylpiperazine of the present disclosure may be further characterized by an X-ray diffractogram as in FIG. 3.

In another embodiment, the coformer is 2,3,5-trimethylpirazine, and the cocrystal of pterostilbene and 2,3,5-trimethylpirazine is characterized by having an X-ray powder diffractogram that comprises characteristic peaks at approximately 13.4 and 25.9±0.3 degrees 2 theta (Cu-$K_\alpha$ radiation, λ=1.5418 Å). Particularly, the cocrystal of pterostilbene and 2,3,5-trimethylpirazine of the present disclosure is characterized by having an X-ray powder diffractogram that comprises further characteristic peaks at 11.4, 22.7 and 26.9±0.3 degrees 2 theta (Cu-$K_\alpha$ radiation, λ=1.5418 Å). More particularly, the molar ratio of pterostilbene and 2,3,5-trimethylpirazine is 2:1.

More specifically, the cocrystal of pterostilbene and 2,3,5-trimethylpirazine is characterized by exhibiting in the X-ray powder diffractogram a pattern of peaks, expressed in 2 theta units in degrees, 2θ (°), which is shown in Table 4.

TABLE 4

| List of selected peaks (only peaks with relative intensity greater than or equal to 1% are indicated): | |
|---|---|
| Pos. [°2Th.] | Rel. Int. [%] |
| 10.7026 | 18.75 |
| 11.3585 | 61.1 |
| 11.7648 | 27.96 |
| 12.8156 | 28.31 |
| 13.4444 | 78.59 |
| 13.5684 | 41.14 |
| 14.2798 | 37.2 |
| 14.9221 | 24.32 |
| 15.1696 | 17.84 |
| 15.7685 | 32.26 |
| 15.9571 | 39.6 |
| 17.2914 | 19.76 |
| 18.7415 | 21.64 |
| 18.9979 | 17.25 |
| 19.2373 | 32.04 |
| 19.4689 | 8.92 |
| 20.0074 | 11.06 |
| 20.7256 | 10.55 |
| 22.5371 | 7.56 |
| 22.7423 | 39.05 |
| 22.9157 | 12.55 |
| 24.1122 | 24.45 |
| 24.6101 | 57.17 |
| 24.9353 | 13.75 |
| 25.8607 | 100 |
| 26.2228 | 39.92 |
| 26.8841 | 44.7 |
| 27.6633 | 9.79 |
| 29.5435 | 10.23 |

The data of the structure of the cocrystal of pterostilbene and 2,3,5-trimethylpirazine defined above obtained by single crystal X-ray diffraction correspond to a cocrystal and are shown below:

| Structure | cocrystal pterostilbene: 2,3,5-trimethylpirazine |
|---|---|
| Temperature (K) | 100(2) |
| Wavelength (Å) | 0.71073 |
| Crystal system | Triclinic |
| space group | P-1 |
| a, b, c (Å) | 7.9098(9), 9.2397(10), 23.359(3) |
| α, β, γ (°) | 83.699(5), 88.189(5), 79.189(5) |
| Volume ($Å^3$) | 1666.6(3) |
| Z, Density (calc.) ($Mg/m^3$) | 2, 1.265 |
| Final R indices [l > 2σ(l)] | R1 = 0.0759, wR2 = 0.1397 |

Figure 4:
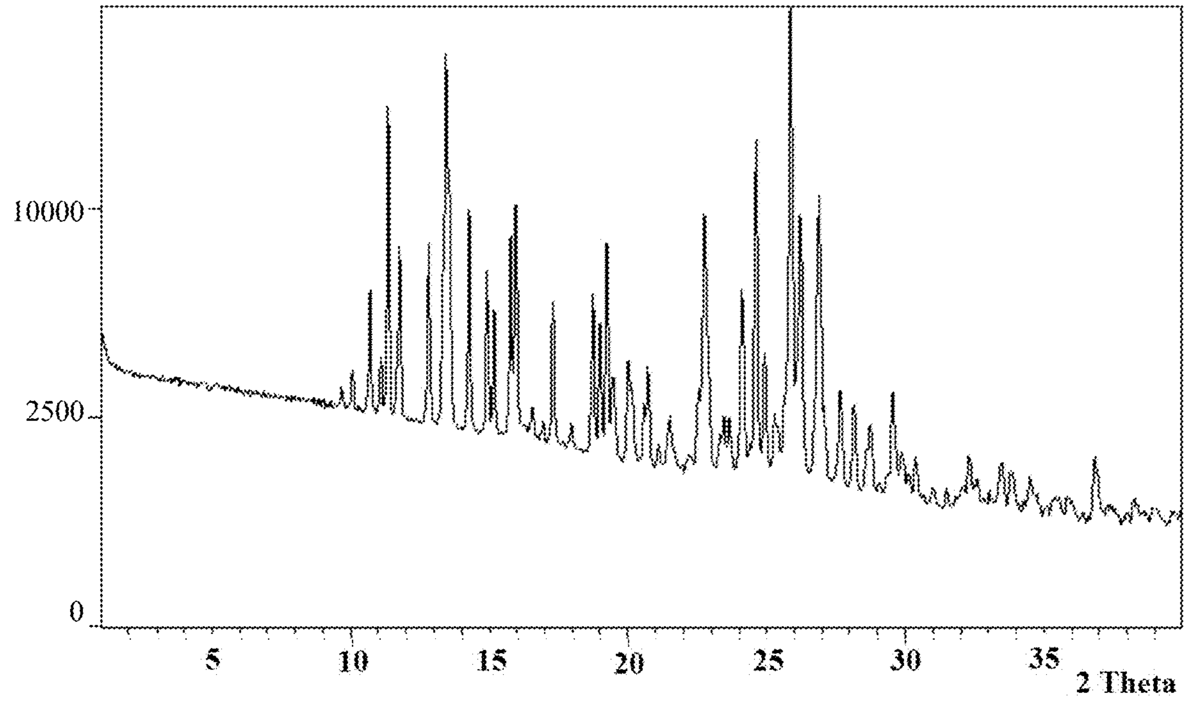
FIG. 4 shows the XRPD of cocrystal of pterostilbene and 2,3,5-trimethylpirazine (2:1).

The cocrystal of pterostilbene and 2,3,5-trimethylpirazine of the present disclosure may be further characterized by an X-ray diffractogram as in FIG. 4.

In another embodiment, the coformer is theophylline and the cocrystal of pterostilbene and theophylline is characterized by having an X-ray powder diffractogram that comprises characteristic peaks at approximately 8.5 and 11.7±0.3 degrees 2 theta (Cu-$K_\alpha$ radiation, λ=1.5418 Å). Particularly, the cocrystal of pterostilbene and theophylline of the present disclosure is characterized by having an X-ray powder diffractogram that comprises further characteristic peaks at 13.7, 15.0 and 16.7±0.3 degrees 2 theta (Cu-$K_\alpha$ radiation, λ=1.5418 Å). More particularly, the molar ratio of pterostilbene:theophylline is 1:1.

More specifically, the cocrystal of pterostilbene and theophylline of the present disclosure is characterized by exhibiting in the X-ray powder diffractogram a pattern of peaks, expressed in 2 theta units in degrees, 2θ (°), which is shown in Table 5.

TABLE 5

| List of selected peaks (only peaks with relative intensity greater than or equal to 1% are indicated): | |
|---|---|
| Pos. [°2Th.] | Rel. Int. [%] |
| 7.895 | 6.3 |
| 8.5374 | 75.42 |
| 9.539 | 21.94 |
| 10.345 | 11.12 |
| 11.72 | 77.78 |
| 12.3861 | 16.26 |
| 13.308 | 35.4 |
| 13.7097 | 74.73 |
| 14.964 | 63.06 |
| 15.1593 | 8.06 |
| 16.0161 | 22.46 |
| 16.6828 | 35.92 |
| 17.1242 | 1.14 |
| 17.4528 | 11.04 |
| 17.8034 | 29.45 |
| 18.2041 | 1.73 |
| 21.5624 | 29.17 |
| 22.2724 | 4.16 |
| 22.4913 | 25.3 |
| 22.8248 | 13.96 |
| 25.8066 | 21.21 |
| 26.0411 | 100 |
| 27.1766 | 27.36 |
| 28.2563 | 17.41 |
| 28.7241 | 8.29 |
| 29.1566 | 5.13 |
| 29.8778 | 2.46 |
| 30.1989 | 3.33 |

In another embodiment, the coformer is theophylline and the cocrystal of pterostilbene and theophylline is in the form of a dichloromethane solvate and is characterized by having an X-ray powder diffractogram that comprises characteristic peaks at approximately 13.4 and 26.0±0.3 degrees 2 theta (Cu-$K_{\alpha}$ radiation. λ=1.5418 Å).

Particularly. the dichloromethane solvate cocrystal of pterostilbene and theophylline of the present disclosure is characterized by having an X-ray powder diffractogram that comprises further characteristic peaks at 10.8. 14.4 and 23.5±0.3 degrees 2 theta (Cu-$K_{\alpha}$ radiation. λ=1.5418 Å). More particularly, the molar ratio of pterostilbene:theophylline:dichloromethane is 1:1:1.

More specifically, the cocrystal pterostilbene:theophylline:dichloromethane solvate of the present disclosure is characterized by exhibiting in the X-ray powder diffractogram a pattern of peaks. expressed in 2 theta units in degrees. 2θ (°). which is shown in Table 6.

TABLE 6

| List of selected peaks (only peaks with relative intensity greater than or equal to 1% are indicated): | |
|---|---|
| Pos. [°2Th.] | Rel. Int. [%] |
| 9.0203 | 15.63 |
| 9.6582 | 6.78 |
| 10.8031 | 53.14 |
| 11.1789 | 4.34 |
| 13.4134 | 62.21 |
| 14.4273 | 25.99 |
| 15.4859 | 5.7 |
| 16.1682 | 3.17 |
| 17.1523 | 3.91 |
| 17.5292 | 7.43 |
| 18.5542 | 6.41 |
| 19.3091 | 6.13 |
| 19.7023 | 3.1 |
| 20.2763 | 6.51 |
| 20.7376 | 2.63 |
| 21.7199 | 12.27 |
| 22.4834 | 2.31 |
| 23.2125 | 6.07 |
| 23.5156 | 26.93 |
| 24.59 | 5.01 |
| 24.9349 | 6.65 |
| 25.6336 | 14.52 |
| 25.9533 | 100 |
| 26.2521 | 9.71 |
| 27.6609 | 2.68 |
| 29.0974 | 4.2 |
| 29.3564 | 2.78 |
| 31.5963 | 2.7 |
| 32.6397 | 2.95 |

The data of the structure of the cocrystal pterostilbene: theophylline:dichloromethane solvate defined above obtained by single crystal X-ray diffraction correspond to a cocrystal and are shown below:

| Structure | cocrystal pterostilbene: theophylline: dichloromethane solvate |
|---|---|
| Temperature (K) | 100(2) |
| Wavelength (Å) | 0.71073 |
| Crystal system | Monoclinic |
| space group | C 2/c |
| a, b, c (Å) | 20.0576(10), 10.1851(5), 25.6891(11) |
| α, β, γ (°) | 90, 106.925(2) ,90 |
| Volume ($Å^3$) | 5020.7(4) |
| Z, Density (calc.) ($Mg/m^3$) | 8, 1.380 |
| Final R indices [I > 2σ(I)] | R1 = 0.0359, wR2 = 0.0814 |

Figure 5:
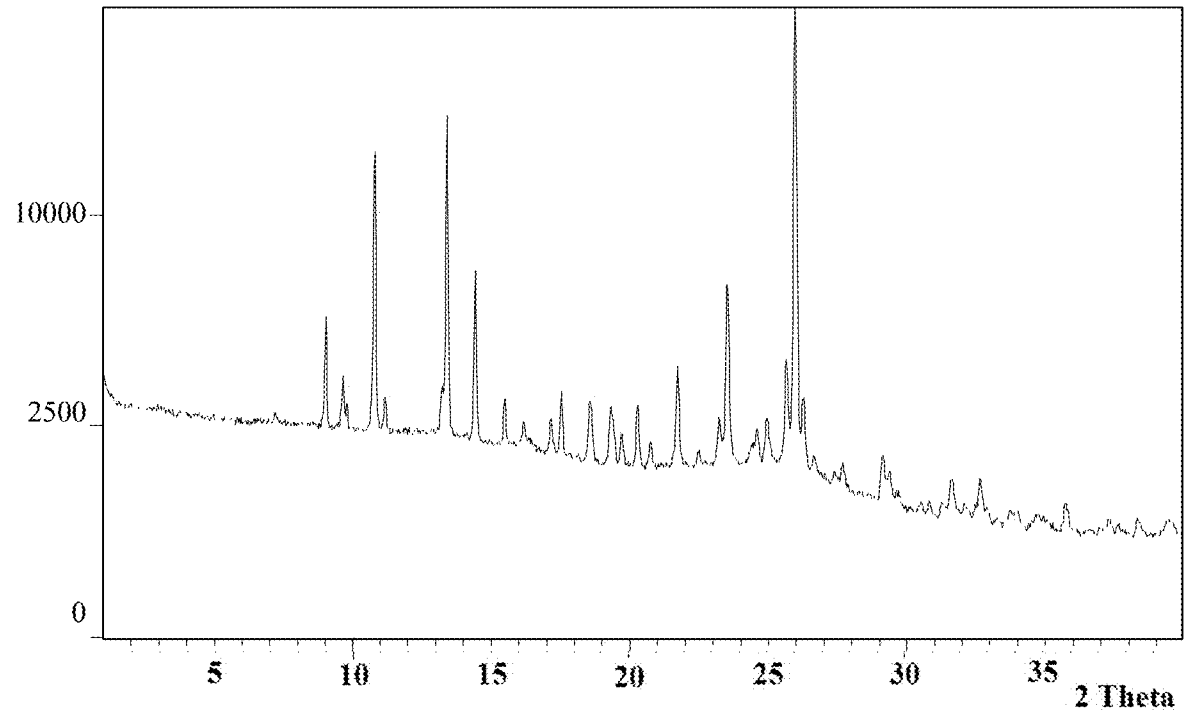
FIG. 5 shows the XRPD of cocrystal of pterostilbene: theophylline:dichloromethane (1:1:1).

The cocrystal pterostilbene:theophylline:dichloromethane solvate of the present disclosure may be further characterized by an X-ray diffractogram as in FIG. 5.

In another embodiment, the coformer is 1,4,8,11-tetrazacyclohexandecane and the cocrystal of pterostilbene and 1,4,8,11-tetrazacyclohexandecane is characterized by having an X-ray powder diffractogram that comprises characteristic peaks at approximately 10.8 and 23.6±0.3 degrees 2 theta (Cu-$K_{\alpha}$ radiation, λ=1.5418 Å).

Particularly, the cocrystal of pterostilbene and 1,4,8,11-tetrazacyclohexandecane of the present disclosure is characterized by having an X-ray powder diffractogram that comprises further characteristic peaks at 16.2, 18.0 and 20.6±0.3 degrees 2 theta (Cu-$K_{\alpha}$ radiation, λ=1.5418 Å). More particularly, the molar ratio of pterostilbene to 1,4,8,11-tetrazacyclohexandecane is 2:1.

More specifically, the cocrystal of pterostilbene and 1,4,8,11-tetrazacyclohexandecane of the present disclosure is characterized by exhibiting in the X-ray powder diffractogram a pattern of peaks, expressed in 2 theta units in degrees, 2θ (°), which is shown in Table 7.

TABLE 7

| List of selected peaks (only peaks with relative intensity greater than or equal to 1% are indicated): | |
|---|---|
| Pos. [°2Th.] | Rel. Int. [%] |
| 8.9629 | 7.86 |
| 10.7628 | 100 |

TABLE 7-continued

| List of selected peaks (only peaks with relative intensity greater than or equal to 1% are indicated): | |
|---|---|
| Pos. [°2Th.] | Rel. Int. [%] |
| 11.8218 | 8.45 |
| 13.2946 | 6.42 |
| 13.9272 | 4.32 |
| 16.2046 | 17.63 |
| 17.5864 | 8.2 |
| 17.8118 | 9.11 |
| 17.9834 | 49.51 |
| 18.6893 | 6.49 |
| 19.2517 | 13.59 |
| 19.4515 | 22.88 |
| 20.2992 | 20.72 |
| 20.5574 | 34.98 |
| 21.2215 | 14.59 |
| 21.6135 | 11.4 |
| 22.8048 | 12.95 |
| 23.1712 | 31.19 |
| 23.5855 | 63.28 |
| 23.9207 | 8.97 |
| 24.4773 | 26.94 |
| 25.8975 | 24.57 |
| 26.5893 | 17.77 |
| 27.1063 | 5.05 |
| 27.5379 | 6.91 |

The data of the structure of the cocrystal of pterostilbene and 1,4,8,11-tetrazacyclohexandecane defined above obtained by single crystal X-ray diffraction correspond to a cocrystal and are shown below:

| Structure | cocrystal pterostilbene:1,4,8,11-tetrazacyclohexandecane |
|---|---|
| Temperature (K) | 100(2) |
| Wavelength (Å) | 0.71073 |
| Crystal system | Monoclinic |
| space group | $P2_1/n$ |
| a, b, c (Å) | 8.4888(3), 11.2401(5), 19.8309(9) |
| α, β, γ (°) | 90, 95.955(2), 90 |
| Volume ($Å^3$) | 1881.95(14) |
| Z, Density (calc.) ($Mg/m^3$) | 4, 1.258 |
| Final R indices [I > 2σ(I)] | R1 = 0.0437, wR2 = 0.1049 |

Figure 6:
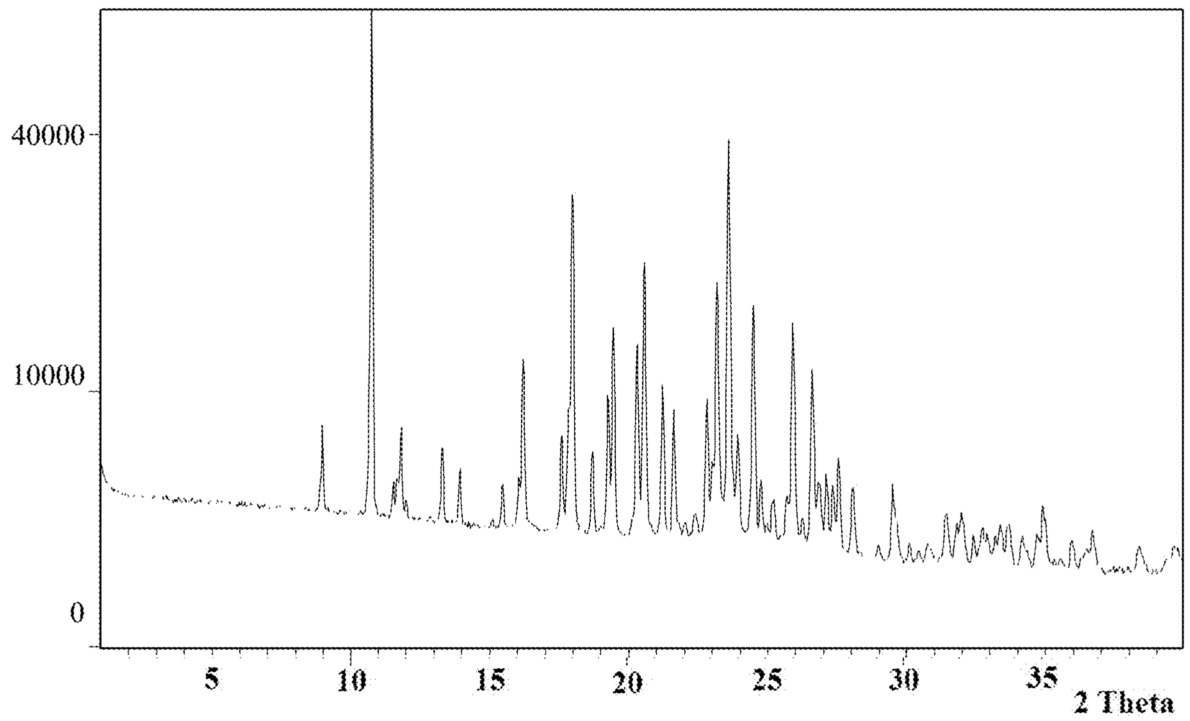
FIG. 6 shows the XRPD of cocrystal of pterostilbene and 1,4,8,11-tetrazacyclohexandecane (2:1).

The cocrystal of pterostilbene and 1,4,8,11-tetrazacyclohexandecane of the present disclosure may be further characterized by an X-ray diffractogram as in FIG. 6.

In another embodiment, the coformer is ethylendiamine and the cocrystal of pterostilbene and ethylendiamine is an anhydre cocrystal characterized by having an X-ray powder diffractogram that comprises characteristic peaks at approximately 14.3 and 19.3±0.3 degrees 2 theta (Cu-$K_\alpha$ radiation, λ=1.5418 Å). Particularly, the cocrystal of pterostilbene and ethylendiamine of the present disclosure is characterized by having an X-ray powder diffractogram that comprises further characteristic peaks at 6.7, 13.4 and 22.0±0.3 degrees 2 theta (Cu-$K_\alpha$ radiation, λ=1.5418 Å). More particularly, the molar ratio of pterostilbene and ethylendiamine is 2:1.

More specifically, the anhydre cocrystal of pterostilbene and ethylendiamine of the present disclosure is characterized by exhibiting in the X-ray powder diffractogram a pattern of peaks, expressed in 2 theta units in degrees, 2θ (°), which is shown in Table 8.

TABLE 8

| List of selected peaks (only peaks with relative intensity greater than or equal to 1% are indicated): | |
|---|---|
| Pos. [°2Th.] | Rel. Int. [%] |
| 6.6926 | 28.17 |
| 7.7966 | 4.85 |
| 11.1893 | 15.31 |
| 13.4421 | 28.42 |
| 14.2703 | 100 |
| 17.3612 | 4.75 |
| 18.1561 | 18.6 |
| 18.3322 | 14.19 |
| 18.8099 | 15.7 |
| 19.3235 | 54.2 |
| 20.314 | 7.61 |
| 20.6456 | 9.02 |
| 21.7635 | 3.78 |
| 22.023 | 38.13 |
| 22.5143 | 5.52 |
| 23.0457 | 10.35 |
| 23.236 | 11.7 |
| 23.3786 | 9.98 |
| 23.997 | 4.47 |
| 24.1765 | 8.76 |
| 25.0016 | 18.12 |
| 25.4203 | 4.2 |
| 25.7345 | 6.3 |
| 26.2684 | 5.49 |
| 26.5054 | 13.19 |
| 26.634 | 10.26 |
| 27.0518 | 1.15 |
| 28.367 | 4.63 |
| 28.7839 | 10.26 |

The data of the structure of the cocrystal of pterostilbene and ethylendiamine defined above obtained by single crystal X-ray diffraction correspond to a cocrystal and are shown below:

| Structure | cocrystal pterostilbene:ethylendiamine |
|---|---|
| Temperature (K) | 100(2) |
| Wavelength (Å) | 0.71073 |
| Crystal system | Monoclinic |
| space group | $P2_1/n$ |
| a, b, c (Å) | 11.3119(3), 5.13890(10), 26.6010(8) |
| α, β, γ (°) | 90, 101.0990(10), 90 |
| Volume ($Å^3$) | 1517.41(7) |
| Z, Density (calc.) ($Mg/m^3$) | 4, 1.253 |
| Final R indices [I > 2σ(I)] | R1 = 0.0375, wR2 = 0.0912 |

Figure 7:
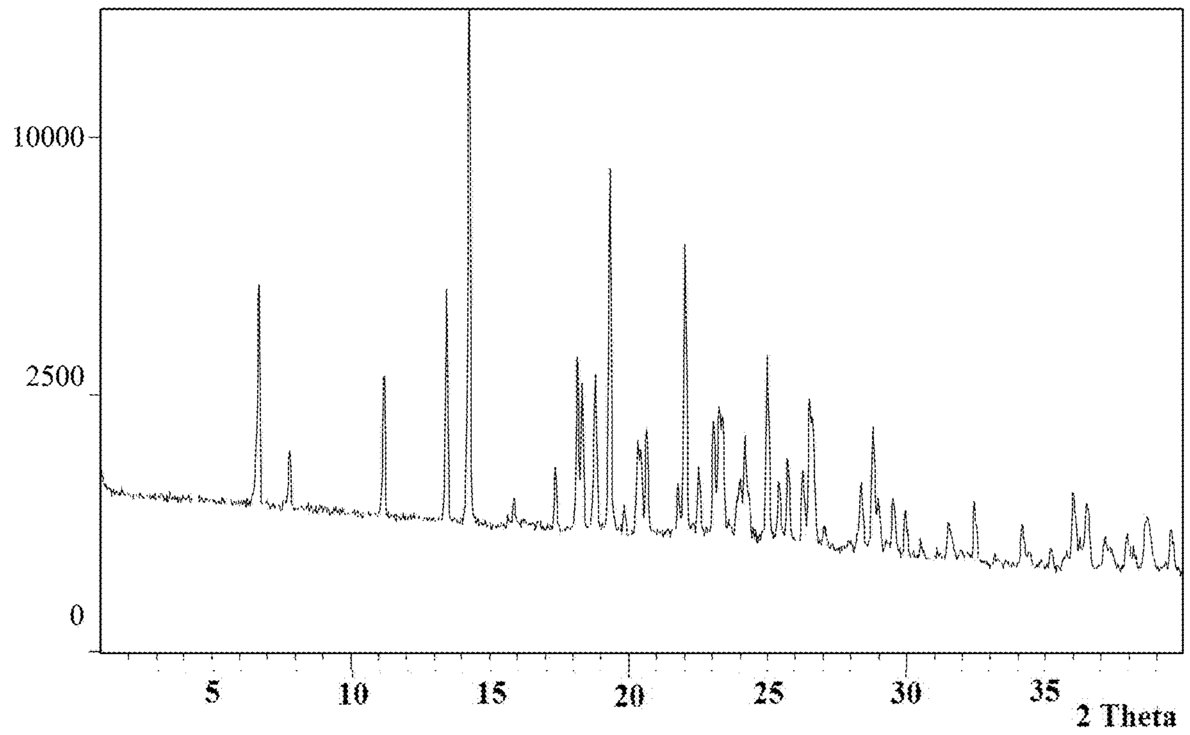
FIG. 7 shows the XRPD of an anhydre cocrystal of pterostilbene and ethylendiamine (2:1).

The cocrystal of pterostilbene and ethylendiamine of the present disclosure may be further characterized by an X-ray diffractogram as in FIG. 7.

In another embodiment, the coformer is ethylendiamine and the cocrystal of pterostilbene and ethylendiamine is a hydrate cocrystal characterized by having an X-ray powder diffractogram that comprises characteristic peaks at approximately 14.3 and 19.3±0.3 degrees 2 theta (Cu-$K_\alpha$ radiation, λ=1.5418 Å). Particularly, the hydrate cocrystal of pterostilbene and ethylendiamine of the present disclosure is characterized by having an X-ray powder diffractogram that comprises further characteristic peaks at 17.5, 21.5, 23.6 and 29.3±0.3 degrees 2 theta (Cu-$K_\alpha$ radiation, λ=1.5418 Å). More particularly, the cocrystal of pterostilbene and ethylendiamine is a hydrate and the molar ratio of of pterostilbene, ethylendiamine and water is 2:1:2.

More specifically, the hydrate cocrystal of pterostilbene and ethylendiamine of the present disclosure is characterized by exhibiting in the X-ray powder diffractogram a pattern of peaks, expressed in 2 theta units in degrees, 2θ (°), which is shown in Table 9.

TABLE 9

| List of selected peaks (only peaks with relative intensity greater than or equal to 1% are indicated): | |
|---|---|
| Pos. [°2Th.] | Rel. Int. [%] |
| 6.7116 | 33.51 |
| 7.8161 | 16.76 |
| 11.2092 | 42.75 |
| 13.4537 | 31.09 |
| 14.2794 | 100 |
| 17.5314 | 14.61 |
| 18.1697 | 62.68 |
| 18.3304 | 14.84 |
| 18.8132 | 20.19 |
| 19.3229 | 74.16 |
| 20.3203 | 6.85 |
| 20.4393 | 10.44 |
| 20.6459 | 9.67 |
| 21.5034 | 3.50 |
| 22.0221 | 54.51 |
| 22.0864 | 28.28 |
| 22.4198 | 13.8 |
| 22.5242 | 16.97 |
| 23.0508 | 18.99 |
| 23.2263 | 17.83 |
| 23.3769 | 16.08 |
| 23.6004 | 2.62 |
| 24.1779 | 12.92 |
| 25.0059 | 39.54 |
| 25.0818 | 18.86 |
| 25.7426 | 20.63 |
| 25.8193 | 9.5 |
| 26.5194 | 27.03 |
| 26.6131 | 15.23 |
| 27.9239 | 1.29 |
| 28.3759 | 9.46 |
| 28.7932 | 14.36 |
| 29.2845 | 6.31 |

Figure 8:
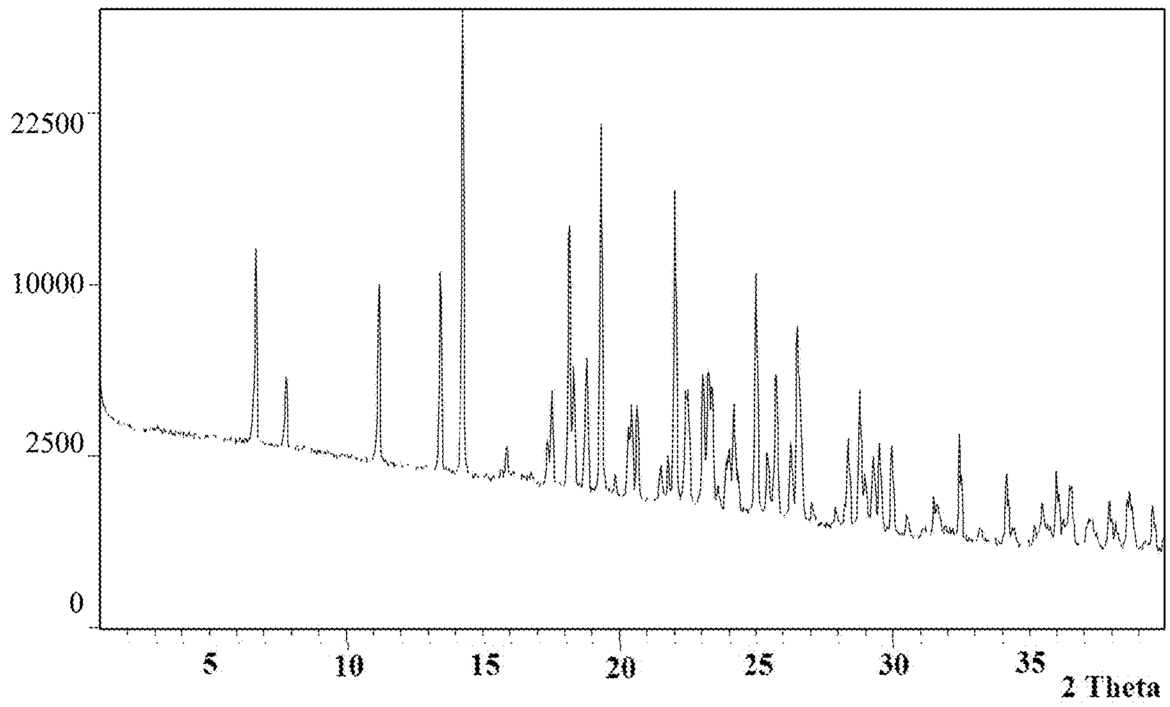
FIG. 8 shows the XRPD of the hydrate cocrystal of pterostilbene and ethylendiamine (2:1:2).

The hydrate cocrystal of pterostilbene and ethylendiamine of the present disclosure may be further characterized by an X-ray diffractogram as in FIG. 8.

In another embodiment, the coformer is 1,4-diazabicyclo [2.2.2]octane (DABCO) and the cocrystal of pterostilbene and DABCO is characterized by having an X-ray powder diffractogram that comprises characteristic peaks at approximately 17.9 and 21.7±0.3 degrees 2 theta (Cu-$K_\alpha$ radiation, λ=1.5418 Å). In an embodiment, the cocrystal of pterostilbene and DABCO of the present disclosure is characterized by having an X-ray powder diffractogram that comprises further characteristic peaks at 10.6, 16.0 and 19.0±0.3 degrees 2 theta (Cu-$K_\alpha$ radiation, λ=1.5418 Å). More particularly, the molar ratio of pterostilbene and DABCO is 2:1.

More specifically, the cocrystal of pterostilbene and DABCO of the present disclosure is characterized by exhibiting in the X-ray powder diffractogram a pattern of peaks, expressed in 2 theta units in degrees, 2θ (°), which is shown in Table 10.

TABLE 10

| List of selected peaks (only peaks with relative intensity greater than or equal to 1% are indicated): | |
|---|---|
| Pos. [°2Th.] | Rel. Int. [%] |
| 3.5114 | 12.83 |
| 10.5515 | 40.18 |
| 13.0566 | 16.22 |
| 13.439 | 41.66 |
| 14.0833 | 26.42 |
| 15.6937 | 10.21 |
| 16.0148 | 84.46 |
| 16.2975 | 36.61 |

TABLE 10-continued

| List of selected peaks (only peaks with relative intensity greater than or equal to 1% are indicated): | |
|---|---|
| Pos. [°2Th.] | Rel. Int. [%] |
| 16.506 | 16.68 |
| 16.694 | 25.28 |
| 17.7479 | 54.75 |
| 17.9298 | 98.33 |
| 18.7258 | 15.6 |
| 18.9506 | 45.82 |
| 19.3364 | 12.74 |
| 19.523 | 12.98 |
| 20.5157 | 36.86 |
| 21.064 | 31.89 |
| 21.5016 | 40.27 |
| 21.7096 | 100 |
| 22.4885 | 37.98 |
| 22.7991 | 14.57 |
| 23.5353 | 12.48 |
| 23.9618 | 14.15 |
| 24.2328 | 25.19 |
| 26.4565 | 20.8 |
| 27.646 | 13.07 |
| 27.9424 | 14.47 |
| 29.1937 | 12.43 |

The data of the structure of the cocrystal of pterostilbene and DABCO defined above obtained by single crystal X-ray diffraction correspond to a cocrystal and are shown below:

| Structure | cocrystal pterostilbene:DABCO |
|---|---|
| Temperature (K) | 100(2) |
| Wavelength (Å) | 0.71073 |
| Crystal system | Monoclinic |
| space group | $P2_1/n$ |
| a, b, c (Å) | 27.1201(16), 6.1642(4), 21.6656(13) |
| α, β, γ (°) | 90, 112.389(2), 90 |
| Volume (Å$^3$) | 3348.9(4) |
| Z, Density (calc.) (Mg/m$^3$) | 4, 1.239 |
| Final R indices [I > 2σ(I)] | R1 = 0.0779, wR2 = 0.2067 |

Figure 9:
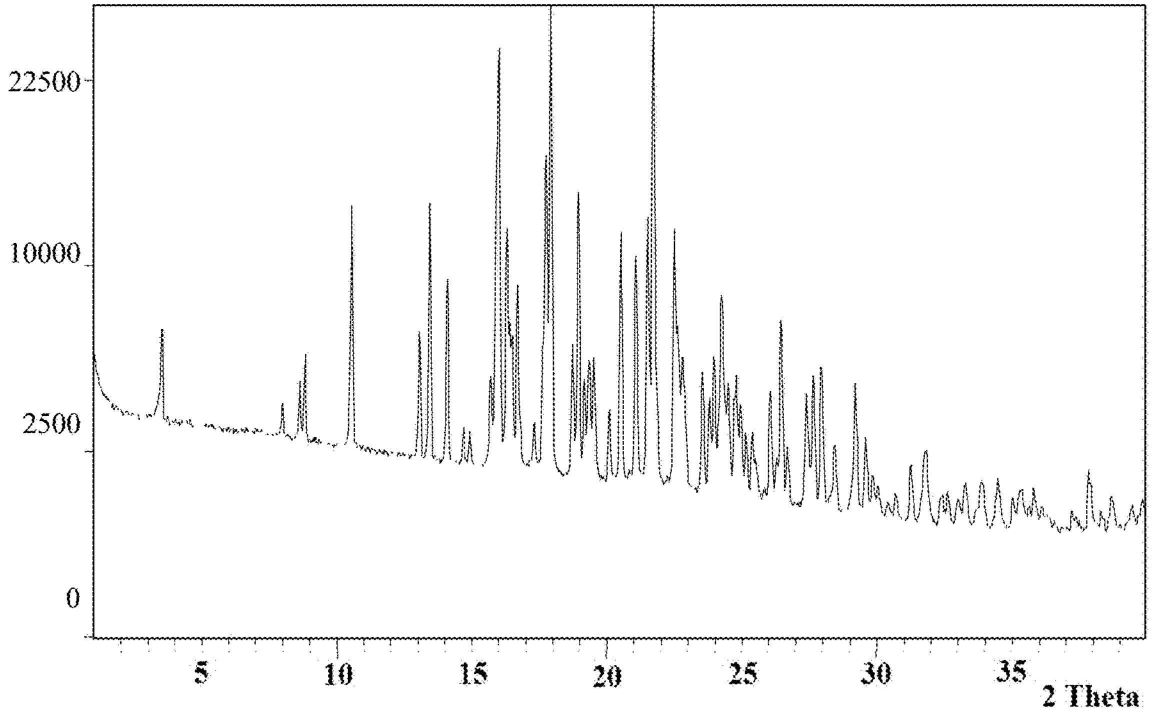
FIG. 9 shows the XRPD of cocrystal of pterostilbene and 1,4-diazabicyclo[2.2.2]octane (DABCO) (2:1).

The cocrystal of pterostilbene and DABCO of the present disclosure may be further characterized by an X-ray diffractogram as in FIG. 9.

In another embodiment, the coformer is 2,4-dihydroxybenzoic acid, and the cocrystal of pterostilbene and 2,4-dihydroxybenzoic acid is characterized by having an X-ray powder diffractogram that comprises characteristic peaks at approximately 11.3 and 27.9±0.3 degrees 2 theta (Cu-$K_\alpha$ radiation, λ=1.5418 Å). Particularly, the cocrystal of pterostilbene and 2,4-dihydroxybenzoic acid is characterized by having an X-ray powder diffractogram that comprises further characteristic peaks at 13.2, 13.3 and 15.8±0.3 degrees 2 theta (Cu-$K_\alpha$ radiation, λ=1.5418).

More specifically, the cocrystal of pterostilbene and 2,4-dihydroxybenzoic acid of the present disclosure is characterized by exhibiting in the X-ray powder diffractogram a pattern of peaks, expressed in 2 theta units in degrees, 2θ (°), which is shown in Table 11 (only peaks with relative intensity greater than or equal to 1% are shown).

TABLE 11

| Pos. [°2Th.] | Rel. Int. [%] |
|---|---|
| 9.1208 | 5.19 |
| 11.2686 | 100 |
| 13.2004 | 15.47 |
| 13.3474 | 10.56 |

TABLE 11-continued

| Pos. [°2Th.] | Rel. Int. [%] |
|---|---|
| 15.8321 | 15.68 |
| 27.8664 | 58.8 |
| 28.6879 | 2.94 |

In another embodiment, the coformer is indole, and the cocrystal of pterostilbene and indole is characterized by having an X-ray powder diffractogram that comprises characteristic peaks at approximately 10.8 and 18.0±0.3 degrees 2 theta (Cu-$K_\alpha$ radiation, λ=1.5418 Å). Particularly, the cocrystal of pterostilbene and indole is characterized by having an X-ray powder diffractogram that comprises further characteristic peaks at 16.3, 20.6 and 23.7±0.3 degrees 2 theta (Cu-$K_\alpha$ radiation, λ=1.5418 Å).

More specifically, the cocrystal of pterostilbene and indole of the present disclosure is characterized by exhibiting in the X-ray powder diffractogram a pattern of peaks, expressed in 2 theta units in degrees, 2θ (°), which is shown in Table 12 (only peaks with relative intensity greater than or equal to 1% are shown).

TABLE 12

| Pos. [°2Th.] | Rel. Int. [%] |
|---|---|
| 10.8127 | 100 |
| 13.3149 | 4.6 |
| 16.2541 | 31.2 |
| 17.634 | 14.73 |
| 18.0393 | 79.59 |
| 18.7211 | 12.17 |
| 20.6195 | 48.43 |
| 21.2805 | 21.97 |
| 21.6648 | 20.36 |
| 23.2261 | 37.01 |
| 23.652 | 85.61 |
| 23.9805 | 14.12 |
| 24.5374 | 29.78 |
| 24.8509 | 6.15 |
| 25.27 | 4.89 |
| 25.9634 | 32.14 |
| 26.6578 | 25.61 |
| 26.9455 | 7.28 |
| 27.1738 | 7.76 |
| 27.3954 | 6.82 |
| 27.6082 | 9.54 |
| 28.09 | 4.43 |
| 29.5453 | 7.3 |
| 31.5065 | 4.47 |
| 32.0389 | 5.98 |
| 33.414 | 4.48 |

Figure 10:
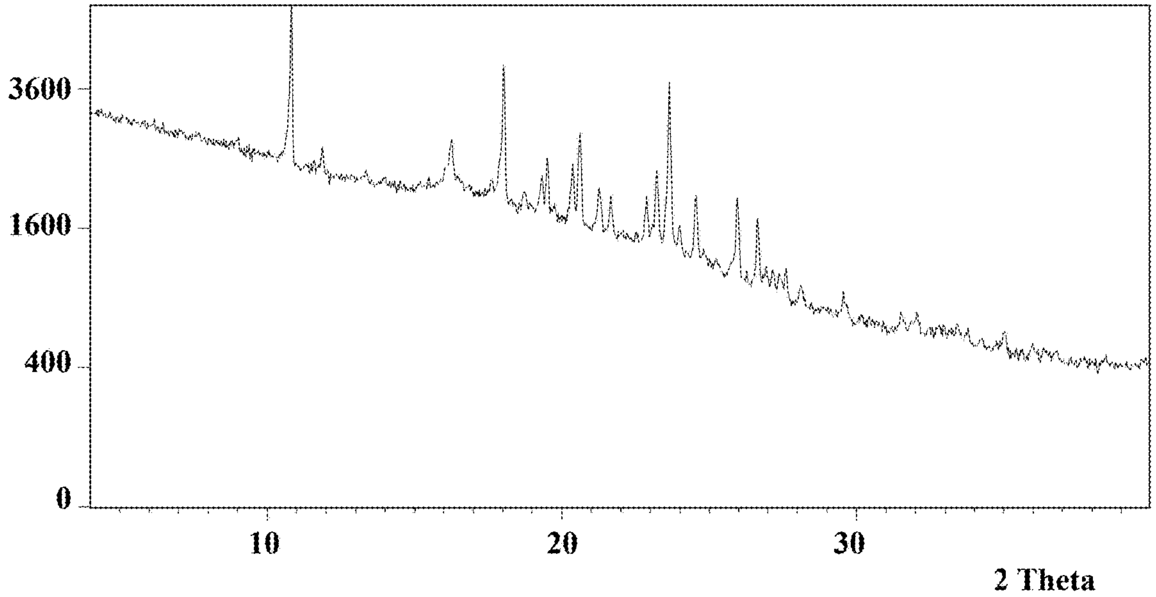
FIG. 10 shows the XRPD of cocrystal of pterostilbene and indole.

The cocrystal of pterostilbene and indole of the present disclosure may be further characterized by an X-ray diffractogram as in FIG. 10.

In another embodiment, the coformer is lysine, and the cocrystal of pterostilbene and lysine is characterized by having an X-ray powder diffractogram that comprises characteristic peaks at approximately 15.5 and 20.0±0.3 degrees 2 theta (Cu-$K_\alpha$ radiation, λ=1.5418 Å). Particularly, the cocrystal of pterostilbene and lysine of the present disclosure is characterized by having an X-ray powder diffractogram that comprises further characteristic peaks at 3.5, 23.6 and 25.7±0.3 degrees 2 theta (Cu-$K_\alpha$ radiation, λ=1.5418 Å).

More specifically, the cocrystal of pterostilbene and lysine of the present disclosure is characterized by exhibiting in the X-ray powder diffractogram a pattern of peaks, expressed in 2 theta units in degrees, 2θ (°), which is shown in Table 13 (only peaks with relative intensity greater than or equal to 1% are shown).

TABLE 13

| Pos. [°2Th.] | Rel. Int. [%] |
|---|---|
| 3.5372 | 58.59 |
| 7.0925 | 12.94 |
| 8.263 | 26.72 |
| 9.3437 | 29.01 |
| 9.8408 | 16.14 |
| 10.6194 | 14.64 |
| 10.9997 | 20.94 |
| 14.0827 | 15.2 |
| 15.4576 | 83.06 |
| 17.732 | 33.82 |
| 17.9985 | 22.34 |
| 18.2017 | 17.84 |
| 18.4432 | 36 |
| 18.7727 | 36.37 |
| 18.9555 | 20.78 |
| 20.0115 | 100 |
| 20.2595 | 54.06 |
| 21.0027 | 15.9 |
| 21.1783 | 27.87 |
| 21.3545 | 32.72 |
| 21.6824 | 17.66 |
| 21.8514 | 19.04 |
| 22.6687 | 30.38 |
| 23.5542 | 79.26 |
| 23.7813 | 22.16 |
| 24.5422 | 29 |
| 24.7264 | 25.04 |
| 24.9756 | 34.11 |
| 25.2936 | 16.76 |
| 25.6522 | 56.34 |
| 25.9003 | 32.12 |
| 26.2167 | 38.92 |
| 26.8416 | 17.9 |
| 27.1881 | 17.92 |

Figure 11:
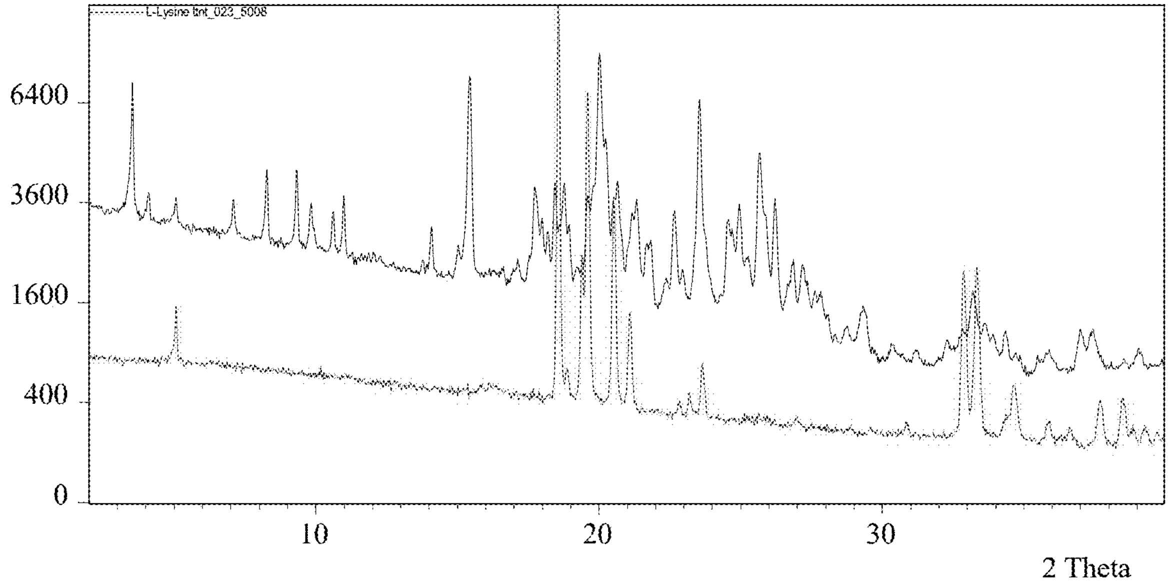
FIG. 11 shows the XRPD of cocrystal of pterostilbene and lysine.

The cocrystal of pterostilbene and lysine of the present disclosure may be further characterized by an X-ray diffractogram as in FIG. 11.

In another embodiment, the coformer is orotic acid, and the cocrystal of pterostilbene and orotic acid is characterized by having an X-ray powder diffractogram that comprises characteristic peaks at approximately 19.3 and 25.5±0.3 degrees 2 theta (Cu-$K_\alpha$ radiation, λ=1.5418 Å). Particularly, the cocrystal of pterostilbene and orotic acid of the invention is characterized by having an X-ray powder diffractogram that comprises further characteristic peaks at 10.7, 16.1 and 20.1±0.3 degrees 2 theta (Cu-$K_\alpha$ radiation, λ=1.5418 Å).

More specifically, the cocrystal of pterostilbene and orotic acid of the present disclosure is characterized by exhibiting in the X-ray powder diffractogram a pattern of peaks, expressed in 2 theta units in degrees, 2θ (°), which is shown in Table 14 (only peaks with relative intensity greater than or equal to 1% are shown).

TABLE 14

| Pos. [°2Th.] | Rel. Int. [%] |
|---|---|
| 3.6034 | 4.21 |
| 9.6181 | 13.7 |
| 10.7456 | 13.13 |
| 12.7087 | 4.66 |
| 13.1924 | 4.45 |
| 15.7259 | 4.68 |
| 16.0899 | 35.29 |
| 16.7439 | 12.99 |
| 16.9612 | 23.52 |
| 17.5256 | 6.42 |
| 18.2323 | 4.08 |
| 18.4244 | 18.03 |
| 19.1095 | 20.12 |
| 19.3097 | 73.08 |

TABLE 14-continued

| Pos. [°2Th.] | Rel. Int. [%] |
|---|---|
| 19.9028 | 12.88 |
| 20.101 | 31.23 |
| 20.6062 | 4.72 |
| 21.1852 | 8.59 |
| 22.3908 | 11.47 |
| 25.5314 | 100 |
| 25.7893 | 13.51 |
| 27.9472 | 4.56 |
| 28.2071 | 4.64 |
| 29.4033 | 2.95 |
| 31.2678 | 3.36 |

Figure 12:
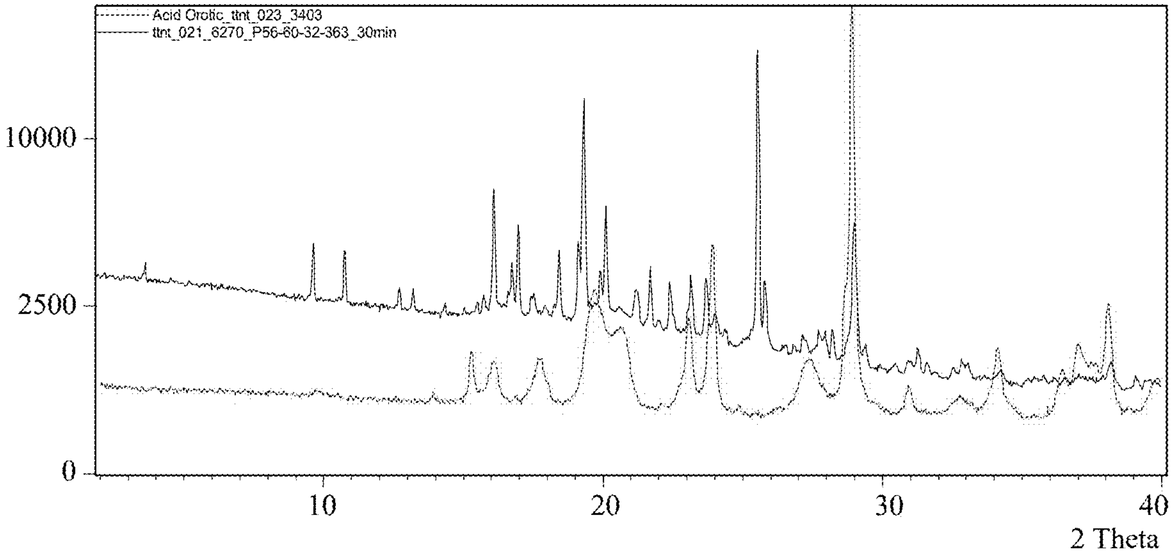
FIG. 12 shows the XRPD of cocrystal of pterostilbene and orotic acid.

The cocrystal of pterostilbene and orotic acid of the present disclosure may be further characterized by an X-ray diffractogram as in FIG. 12.

In another embodiment, the coformer is 1,10-phenanthroline, and the cocrystal of pterostilbene and 1,10-phenanthroline is characterized by having an X-ray powder diffractogram that comprises characteristic peaks at approximately 13.7 and 22.5±0.3 degrees 2 theta (Cu-$K_\alpha$ radiation, λ=1.5418 Å). Particularly, the cocrystal of pterostilbene and 1,10-phenanthroline of the invention is characterized by having an X-ray powder diffractogram that comprises further characteristic peaks at 7.2, 19.0 and 21.4±0.3 degrees 2 theta (Cu-$K_\alpha$ radiation, λ=1.5418 Å).

More specifically, the cocrystal of pterostilbene and 1,10-phenanthroline of the present disclosure is characterized by exhibiting in the X-ray powder diffractogram a pattern of peaks, expressed in 2 theta units in degrees, 2θ (°), which is shown in Table 15 (only peaks with relative intensity greater than or equal to 1% are shown).

TABLE 15

| Pos. [°2Th.] | Rel. Int. [%] |
|---|---|
| 7.2088 | 38.89 |
| 10.1202 | 14.04 |
| 11.038 | 8.68 |
| 12.8944 | 4.97 |
| 13.7324 | 93.49 |
| 13.9119 | 6.09 |
| 14.3282 | 14.65 |
| 15.1864 | 10.29 |
| 16.7281 | 20.31 |
| 17.3629 | 22.96 |
| 18.4054 | 14.8 |
| 18.9752 | 90.45 |
| 19.1867 | 6.22 |
| 19.6921 | 34.77 |
| 20.0142 | 12.73 |
| 20.1685 | 12.37 |
| 20.3687 | 31.96 |
| 21.4046 | 61.45 |
| 21.9649 | 29.47 |
| 22.4824 | 100 |
| 22.9397 | 59.83 |
| 23.164 | 13 |
| 24.6077 | 14.01 |
| 25.2902 | 12.24 |
| 26.2744 | 9.87 |
| 26.6725 | 6.68 |
| 27.3256 | 10.59 |
| 27.7187 | 31.48 |
| 27.9525 | 36.44 |
| 28.408 | 9.75 |
| 30.7515 | 6.41 |

Figure 13:
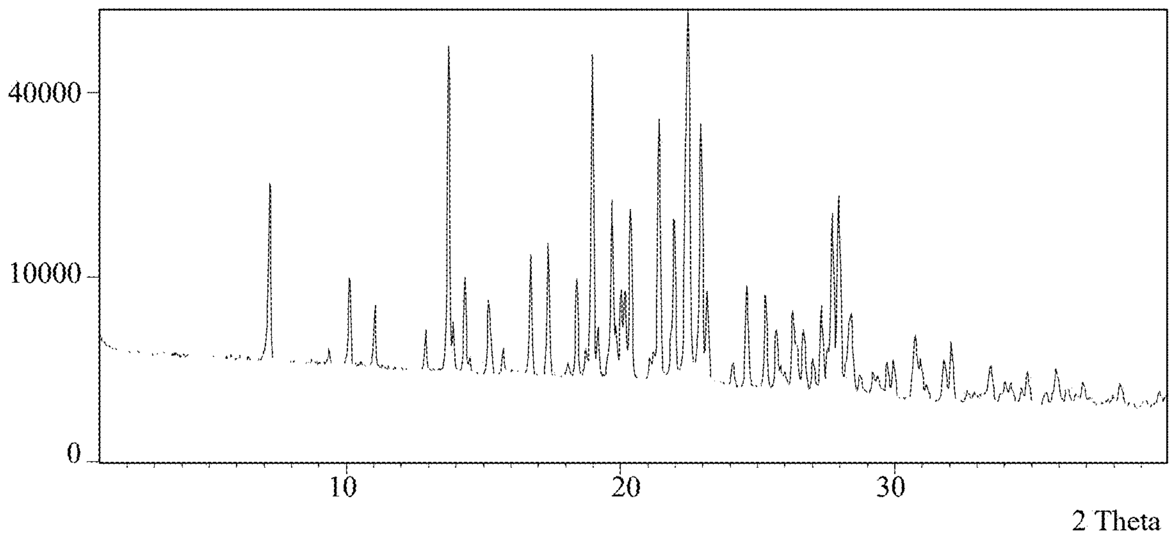
FIG. 13 shows the XRPD of cocrystal of pterostilbene and 1,10-phenanthroline.

The cocrystal of pterostilbene and 1,10-phenanthroline of the present disclosure may be further characterized by an X-ray diffractogram as in FIG. 13.

In another embodiment, the coformer is urea, and the cocrystal of pterostilbene and urea is characterized by having an X-ray powder diffractogram that comprises characteristic peaks at approximately 14.6 and 21.5±0.3 degrees 2 theta (Cu-$K_\alpha$ radiation, λ=1.5418 Å). Particularly, the cocrystal of pterostilbene and urea of the invention is characterized by having an X-ray powder diffractogram that comprises further characteristic peaks at 15.7, 20.1 and 23.3±0.3 degrees 2 theta (Cu-$K_\alpha$ radiation, λ=1.5418 Å).

More specifically, the cocrystal of pterostilbene and urea of the present disclosure is characterized by exhibiting in the X-ray powder diffractogram a pattern of peaks, expressed in 2 theta units in degrees, 2θ (°), which is shown in Table 16 (only peaks with relative intensity greater than or equal to 1% are shown).

TABLE 16

| Pos. [°2Th.] | Rel. Int. [%] |
|---|---|
| 9.1326 | 16.9 |
| 14.4456 | 24.51 |
| 14.6247 | 62.75 |
| 15.6623 | 44.48 |
| 15.8453 | 11.53 |
| 16.4798 | 28.51 |
| 17.5585 | 43.85 |
| 17.8678 | 15.69 |
| 18.2891 | 11.94 |
| 18.714 | 11.63 |
| 20.081 | 70.24 |
| 21.1043 | 32.85 |
| 21.4926 | 100 |
| 23.2553 | 60.86 |
| 25.0127 | 10.52 |
| 25.2546 | 13.54 |
| 25.8663 | 43.67 |
| 26.2836 | 8.76 |
| 28.6094 | 9.42 |
| 28.8096 | 25.83 |
| 29.1012 | 14.81 |
| 29.3163 | 9.05 |
| 29.7263 | 6.85 |
| 31.4451 | 6.47 |
| 32.0163 | 7.5 |

Figure 14:
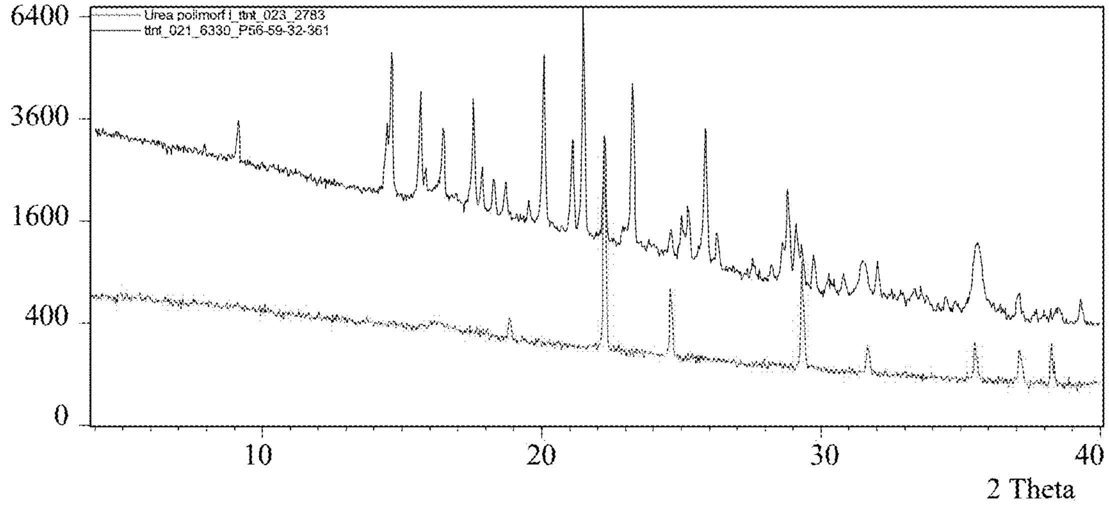
FIG. 14 shows the XRPD of cocrystal of pterostilbene and urea.

The cocrystal of pterostilbene and urea of the present disclosure may be further characterized by an X-ray diffractogram as in FIG. 14.

It is also disclosed Form VI of pterostilbene, which is characterized by having an X-ray 10 powder diffractogram that comprises characteristic peaks at approximately 11.8 and 19.5±0.3 degrees 2 theta (Cu-$K_\alpha$ radiation, λ=1.5418 Å). Particularly, the Form VI of pterostilbene of the present disclosure is characterized by having an X-ray powder diffractogram that comprises further characteristic peaks at 15.3, 23.4 and 25.8±0.3 degrees 2 theta (Cu-$K_\alpha$ radiation, λ=1.5418 Å).

More specifically, Form VI of pterostilbene is characterized by exhibiting in the X-ray powder diffractogram a pattern of peaks, expressed in 2 theta units in degrees, 20 (0), which is shown in Table 17.

TABLE 17

List of selected peaks (only peaks with relative intensity greater than or equal to 1% are indicated):

| Pos. [°2Th.] | Rel. Int. [%] |
|---|---|
| 4.2415 | 5.57 |
| 8.5502 | 10.81 |
| 10.5774 | 13.07 |

TABLE 17-continued

List of selected peaks (only peaks with relative intensity greater than or equal to 1% are indicated):

| Pos. [°2Th.] | Rel. Int. [%] |
|---|---|
| 11.7962 | 61.38 |
| 12.679 | 5.74 |
| 14.4366 | 5.91 |
| 15.2677 | 49.74 |
| 15.7733 | 14.73 |
| 17.1543 | 26.63 |
| 17.544 | 12.49 |
| 17.766 | 11.37 |
| 19.1093 | 20.45 |
| 19.2979 | 47.49 |
| 19.4603 | 100 |
| 20.2995 | 17.98 |
| 20.4558 | 23.57 |
| 21.2784 | 31.03 |
| 22.4938 | 9.61 |
| 23.3938 | 41.8 |
| 23.692 | 29.25 |
| 24.4406 | 9.04 |
| 25.546 | 46.13 |
| 25.7874 | 50.63 |
| 26.4831 | 22.59 |
| 27.2929 | 10.96 |
| 27.5235 | 6.7 |
| 27.7108 | 7.42 |
| 27.8379 | 7.24 |
| 29.4516 | 17.27 |
| 31.4595 | 7.66 |

The data of the structure of Form VI of Pterostilbene defined above obtained by single crystal X-ray diffraction correspond to a polymorph of pterostilbene and are shown below:

| Structure | Form VI of Pterostilbene |
|---|---|
| Temperature (K) | 100(2) |
| Wavelength (Å) | 0.71073 |
| Crystal system | Monoclinic |
| space group | C 2/c |
| a, b, c (Å) | 17.113(9), 7.478(4), 41.58(3) |
| α, β, γ (°) | 90, 98.97(2), 90 |
| Volume ($Å^3$) | 5257(5) |
| Z, Density (calc.) ($Mg/m^3$) | 16, 1.295 |
| Final R indices [$I > 2\sigma(I)$] | R1 = 0.0447, wR2 = 0.1441 |

Figure 15:
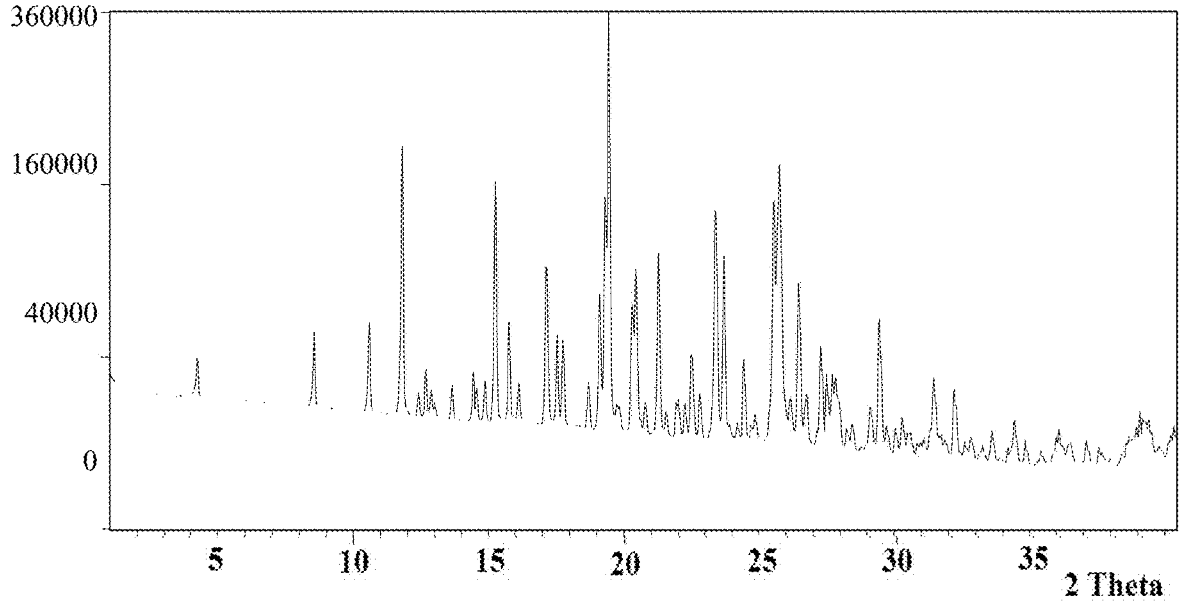
FIG. 15 shows the XRPD of Form VI of pterostilbene.

Form VI of pterostilbene of the present disclosure may be further characterized by an X-ray diffractogram as in FIG. 15.

It is also part of the present disclosure the provision of a process for the preparation of the cocrystal of pterostilbene and a coformer as defined above.

In an example, the process comprises the steps of:

a) mixing pterostilbene and picolinic acid in the presence of toluene as a solvent;

b) stirring the mixture of step a) at room temperature until the cocrystal is formed; and c) isolating the cocrystal thus obtained.

In another example, the process comprises the step of.

a) mixing pterostilbene and the coformer;

b) stirring the mixture of step a) at room temperature until the cocrystal is formed; and c) isolating the cocrystal thus obtained.

In a particular example, the coformer is selected from 1,4-dimethylpiperazine, 2,3,5-trimethylpirazine, and ethylendiamine.

In another example, the process comprises the step of.

a) mixing pterostilbene and dichloromethane, and then adding theophylline to form a suspension;

b) stirring the mixture of step a) at room temperature until the cocrystal is formed;

c) isolating the cocrystal thus obtained; and d) optionally, desolvating the cocrystal by heating.

In another example, the process comprises the step of.

a) mixing pterostilbene and 1,4,8,11-tetrazacyclohexandecane, and the adding theophylline to form a suspension;

b) stirring the mixture of step a) at room temperature until the cocrystal is formed;

c) isolating the cocrystal thus obtained.

In another example, the process comprises the step of.

a) dissolving 1,4-diazabicyclo[2.2.2]octane (DABCO) in xylene and then adding pterostilbene;

b) stirring the mixture of step a) at room temperature until the cocrystal is formed;

c) isolating the cocrystal thus obtained.

Cocrystals of pterostilbene with 2,4-DHBA, indole, lysine, orotic acid, phenanthroline, and urea are obtained as explained below.

The cocrystals of pterostilbene and a coformer as defined above the present disclosure may also be defined by its preparation process. Accordingly, this aspect of the present disclosure can be formulated as the cocrystals of pterostilbene and a coformer as defined above obtainable by the previous processes, optionally including any preferred or particular embodiment of the processes and possible combinations of some of the process features disclosed above.

The second aspect of the present disclosure relates to a composition comprising an effective amount of a cocrystal of pterostilbene and a coformer as defined above together with one or more appropriate acceptable excipients or carriers. It is also disclosed a composition comprising an effective amount of of crystalline Form VI of pterostilbene as defined above together with one or more appropriate acceptable excipients or carriers, such as pharmaceutical composition, a dietary supplement, a cosmetical composition, a functional food or beverage, a premix, a pet food or a medical food composition. The term "effective amount" refers to the amount of the cocrystal which provides a therapeutic effect after its application.

In an embodiment, the composition of the second aspect of the present disclosure is a pharmaceutical composition comprising a pharmaceutically effective amount of a cocrystal of pterostilbene and a coformer as defined above together with one or more appropriate pharmaceutically acceptable excipients or carriers. The term "pharmaceutical composition" refers to a mixture of the cocrystal of pterostilbene disclosed herein with other chemical components, such as diluents or carriers. The pharmaceutical composition facilitates administration of the cocrystal to an organism. Particularly, the pharmaceutical compositon can be formulated for inhaled, intramuscular, subcutaneous, oral, or topical, administration.

In an embodiment, the composition of the second aspect of the present disclosure is a dietary supplement comprising an effective amount of a cocrystal of pterostilbene and a coformer as defined above together with one or more appropriate orally acceptable excipients or carriers. The term "dietary supplement" refers to a product taken orally that contains an ingredient intended to supplement the diet. Dietary supplements can be in form of tablets, capsules, softgels, gelcaps, liquids, powders, bars, drinks, shakes and other food products. As an example, the dietary supplement may be to enhance athletic performance.

The terms "acceptable excipients or carriers" refers to acceptable material, composition or vehicle, such as liquid or solid fillers, diluenst, binders, lubricants, disintegrants, solvents, or encapsulating materials. Each component must be acceptable in the sense of being compatible with the other ingredients of the composition. It must also be suitable for use in contact with the tissue or organ of humans and animals without excessive toxicity, irritation, allergic response, immunogenicity or other problems or complications commensurate with a reasonable benefit/risk ratio. In pharmaceutical compositons the acceptable excipient or carrier is a pharmaceutically acceptable excipient or carrier.

In a particular embodiment, the pharmaceutical composition as defined above further comprises one or more active ingredients selected from the group consisting of antiinflamatory agents, chemotherapeutic agents, immunomodulatory agents, cancer hormone therapeutic agents, targeted cancer therapeutic agents, antidiabetic agents, lipid lowering agents, antiarthritic agents, dementia treatment agents, antiatherosclerotic agents, antiobesity agents, antiosteoporotic agents, and age related diseases agents. In a particular embodiment, the dietary supplement as defined above further comprises one or more active ingredients selected from the group consisting of L-carnitine, xylitol, vitamins, carotenoids, omega-3 fatty acids, flavonoids, coenzime Q10, natural products inhibiting 5-LOX, harpagoside (Figwort or Devil's Claw), copper, zinc, and manganese. The mentioned active ingredients can be in any solid form including possible pharmaceutically acceptable salts, solvates, polymorphs, and cocrystals thereof.

Examples of anti-inflammatory agents include nonsteroidal anti-inflammatory drugs (NSAIDs), such as salicylates including acetylsalicylic acid, diflunisal, salicylic acid and its salts, salsalate; propionic acid derivatives including ibuprofen, dexibuiprofen, naproxen, fenoprofen, ketoprofen, dexketoprofen, flurbiprofen, oxaprozin, loxoprofen; acetic acid derivatives including iondomethacin, tolmetin, sulindac, etodolac, ketorolac, diclofenac, aceclofenac, nabumetone; enolic acid (oxicam) derivatives including piroxicam, meloxicam, tenoxicam, droxicam, lornopxicam, isoxicam, phenylbutazone; anthranilic acid derivatives (fenamates), including mefenamic acid, meclofenamic acid, flufenamic acid, tolfenamic acid; selective COX-2 inhibitors (coxibs) including celecoxib, rofecoxib, valdecoxib, parecoxib, lumiracoxib, etoricoxib, firocoxib; sulfoanilides including nimesulide; clonixin, licofelone; anti-inflammatory agents also include antileukotrienes such as meclofenamate sodium, zileuton; immune selective anti-inflammatory derivatives (ImSAIDs) such as sub mandibular gland peptide-T (SGP-T), tripeptide phenylalanine-glutamine-glycine (FEC) and its D-isomeric form (feG).

Examples of chemotherapeutic agents include alkylating agents, such asmechlorethamine, cyclophosphamide, melphalan, chlorambucil, ifosfamide, busulfan, N-nitroso-N-mdthylurea, carmustine, lomustine, semustine, fotemustine, streptozotocin, dacarbazide, mitozolomide, temozolomide, thiotepa, mitomycin, diaziquone, cisplatin, carboplatin, oxaliplatin, procarbazine, hexamethylmelamine; antimetabolites, such as methotrexate, pemetrexed, fluorouracil, capecitabine, cytarabine, gemcitabine, decitabine, azacytidine, fludarabine, nelarabine, cladribine, clofarabine, pentostatin, thioguanine, mercaptopurine; anti-microtubule agents, such as vincristine, vinblastine, vinorelbine, vindesine, vinflunine, paclitaxel, docetaxel, podophyllotoxin, etoposide, teniposide; topoisomerase inhibitors, such as irinotecan, topotecan, etoposide, doxorubicin, mitoxantrone, teniposide, novobiocin, merbarone, aclarubicin; cytotoxic antibiotics, such as mitomycin C, actinomycin, doxorubicin, daunorubicin, epirubicin, aclarubicin, mitoxantrone, bleomycin; and janus kinase inhibitors such as previously described.

Examples of immunomodulatory agents include ipilimumab, nivolumab, pembrolizumab, atezolizumab, avelumab, durvalumab, cemiplimab, rituximab, oncorine, talimogene, laherparecvec, tisagenlecleucel, axicabtagene, ciloleucel, interferon alpha 2a, interferon alpha 2b, human leukocyte interferon-alpha, interferon beta 1a, interferon beta, 1b, interferon PEGylated versions, interleukin-2, interleukin-7, interleukin-12, chemokine ligand-3, chemokine ligand-26, chemokine ligand-7, BCG vaccine, thalidomide, lenalidomide, pomalidomide, apremilast, cytosine phosphate-guanosine, oligodeoxynucleotides, glucans, and sipuleucel-T vaccine.

Examples of cancer hormone therapeutic agents include tamoxifen, anastrozole, letrozole, exemestane, raloxifene, and fulvestrant.

Examples of targeted cancer therapeutic agents include imatinib, gefitinib, erlotinib, sorafenib, sunitinib, dasatinib, lapatinib, nilotinib, bortezomib, tamoxifen, tofacitinib, crizotinib, obatoclax, navitoclax, gossypol, iniparib, olaparib, perifosine, apatinib, vemurafenib, dabrafenib, trametinib, salinomycin, vintafolide, temsitolimus, everolimus, vemurafenib, trametinib, dabrafenib, prembolizumab, rituximab, trastuzumab, alemtuzumab, cetuximab, panitumumab, bevacizumab, and ipilimumab.

Examples of antidiabetic agents include biguanides (i.e., metformin, buformin, phenformin), sulfonylureas (i.e., acetohexamide, carbutamide, chlorpropamide, glibomuride, gliclazide, glimepiride, glipizide, gliquidone, glisoxepid, glyburide, glybuthiazole, glybuzole, glyhexamide, glymidine, glypinamide, phenbutamide, tolazamide, tolbutamide, tolcyclomide), thiazolidinediones (i.e., piogliatazone, rosiglitazone, troglitazone), beta andrenergic blockers, and other antidiabetics such as acarbose, calcium mesoxalate, miglitol, nateglinide, repaglinide, and voglibose.

Examples of lipid lowering agents include statins, such as atorvastatin, fluvastatin, lovastatin, pitavastatin, pravastatin, rosuvastatin and simvastatin; bile-acid-binding-resins such as cholestyramine, colesevelam, colestipol; cholesterol absorption inhibitors such as ezetimibe; PCSK9 inhibitors such as alirocumab, evolucumab; fibrates such as fenofibraste, gemfibrozil; and niacin.

Examples of antiarthritic agents include painkillers including acetaminophen, tramadol, oxycodone, hydrocodone; nonsteroidal anti-inflammatory drugs (NSAIDs) as previously described; counterirritant creams and ointments containing menthol or capsaicin; disease-modifying antirheumatic drugs (DMARDs) such as methotrexate and hydroxychloroquinone; biologic response modifiers such as tumor necrosis factor (TNF) inhibitors including etanercept, infliximab; interleukin-1 (IL-1), interleukin-6 (IL-6), Janus kinase enzymes, B cells, and T cells.

Example of dementia treatment agents include anti-Alzheimer agents such as cholinesterase inhibitors such as donepezil, galantamine, rivastigmine, tacrine, physostigmine, neostigmine, pyridostigmine, ambenonium, demacarium, caffeine, rosmarinic acid, alpha-pipene, edrophonium, huperize A, ladostigil, ungeremine, lactucopicrin, acotiamide; and NMDA receptor antagonists such as memantine; and of anti-Parkinson agents include carbidopa-levodopa; dopamine agonists, such as pramipexole, ropinirole, rotigotine, apomorphine, lergotrile, pergolide, bromocriptine, lisuride, aripiprazole, phencyclidine, quinpirole, salvinorin A, cabergolide, ciladopa, dihydrexidine, dinapsoline, doxanthrine, epicriptine, piribedil, pramipexole, propylnorapomorphine, quinagolide, roxindole, sumanirole, fenoldopam; MAO B inhibitors such as isocarboxacid, nialamine, phenelzine, hydracarbazine, tranylcypromine, bifemelane, moclobemide, pirlindole, toloxatone, rasagiline, selegiline, safinamide, linezolidbenmoxin, iproclozide, iproniazid, menabazine, octamonix, pheniprazine, phenoxypropazine, pivalylbenzhydrazine, safrazine, caroxazone, minaprine, brofaromine, eprobemide, methylene blue, metralindole, curcumin, harmaline, harmine, amiflamine, befloxatone, cimoxatone, esuprone, sercloremide, tetrindole, CX157; catechol o-methyltransferase (COMT) inhibitors such as entacapone, tolcapone, nebicapone, nitecapone, opicapone; anticholinergics such as benztropine, trihexyphenidyl, clozapine, quetiapine, atropine, biperiden, chlorpheniramine, and certain SSRIs (such as citalopram), Examples of antiatherosclerotic agents include lipid lowering agents as previously described; antiplatelet agents such as irreversible cyclooxygenase inhibitors including aspirin and trifusal, adenosine diphosphate (ADP) receptor inhibitors including cangrelor, clopidogrel, prasugrel, ticagrelor, ticlopidine, phosphodiesterase inhibitors including cilostazol, protease-activated receptor-1 (PAR-1) antagonists including vorapaxar, glycoprotein IIB/IIIA inhibitors including abciximab, eptifibatide, tirofiban, adenosine reuptake inhibitors including dipyridamole, thromboxane inhibitors; nonselective beta blocker agents non selective including propranolol, bucindolol, carteolol, carvedilol, labetalol, nadolol, oxprenolol, penbutolol, pindolol, sotalol, timolol; beta-1 selective beta blocker agents such as acebutolol, atenolol, betaxolol, bisoprolol, celiprolol, metoprolol, nebivolol, esmolol; beta-2 selective beta blocker agents such as butaxamine, ICI-118,551; beta-3 selective beta blocker agents such as SR 59230A; angiotensin-converting enzyme (ACE) inhibitors such as enalapril, ramipril, quinapril, perindopril, lisinopril, benazepril, imidapril, trandolapril, cilazapril, fosinopril, antihypertensive peptides, arfalasin; calcium channel blockers such as; diuretics such as loop diuretics including bumetamide, furosemide, ethacrynic acid, toresamide, thiazides including bendroflumethiazide, hydrochlorothiazide, arginine vasoprerssin receptor 2 antagonists including amphotericin B, lithium, selective vasoprerssin V2 antagonist including tolvaptan, conivaptan, Na—H exchanger antagonists including dopamine, carbonic anhydrase inhibnitors including acetazolamide and dorzolamide, potassium-sparing diuretics including amiloride, spironolactone, eplerenone, triamterene, potassoium canrenoate, xanthines including caffeine, theophylline, theobromine and other diuretics including glucose, mannitol, calcium chloride, and ammonium chloride.

Examples of antiobesity agents include orlistat, cetilistat, lorcasein, sibutramine, rimonabat, metformin, exenatide, liraglutide, semaglutide, amylin, pramlintide, phentermide/topiramate, bupropion/naltrexone, tesofensine, dexfenfluramine, and fenfluramine/phentermine.

Examples of antiosteoporotic agents include bisphosphonates, such as alendronate, risedronate, ibandronate, etidronate, zoledronate or zolendronic acid; teriparatide, abaloparatide and parathyroid hormone, raloxifene, calcitonin, denosumab, strontium ranelate, and hormone replacement-therapy, such as with estrogen.

In a particular embodiment, the cosmetical composition, the dietary supplement, the functional food or beverage, the premix, the animal feed, the pet food, or the medical food composition as defined above further comprises one or more nutraceutical ingredient such as vitamins, carotenoids, omega-3 fatty acids, flavonoids or the like.

Examples of vitamins include but are not limited to Vitamin A (acetate or palmitate, betacarotene), vitamin B1 (thiamine (aneurine)) (hydrochloride or mononitrate), B2 (riboflavin), vitamin B6 (pyridoxine hydrochloride), vitamin B12 (cobalamin), vitamin B12 (cyanocobalamin), vitamin B12 (mecobalamin), vitamin C (ascorbic acid), nicotinic acid, vitamin D2 (ergo-calciferol), vitamin D3 (chole-calciferol), vitamin E (alpha tocopheryl acetate, alpha tocopheryl succinate, alpha tocopherol, γ-tocopherol), vitamin K (phylloquinone, menadione etc), and nicotinamide riboside.

Examples of carotenoids include, but are not limited to, lutein, lycopene, α-carotene, β-carotene, γ-carotene, β-cryptoxanthin, capsanthin, canthaxanthin, zeaxanthin, and astaxanthin.

Examples of omega-3 fatty acids include but are not limited to, alfa-linoleic acid (ALA), eicosapentaenoic acid (EPA) and docosahexaenoic acid (DHA).

Examples of flavonoids include, but are not limited to, kaempferol, myricetin, quercetin, rutin, catechin, epicatechin, ECG, gallocatechin, EGC, EGCG, cyanidin, caffeic acid, theaflavin, theaflavin gallate, luteolin, daidzein, genestein, and glycitein.

Examples of natural products inhibiting 5-LOX include, but are not limited to baicalein, caffeic acid, curcumin, hyperforin, and St John's wort.

The compositions of the present disclosure can be prepared according to methods well known in the state of the art. The appropriate excipients and/or carriers, and their amounts, can readily be determined by those skilled in the art according to the type of formulation being prepared.

All the embodiments disclosed above for the cocrystals of pterostilbene as defined above also applies to the compositions of the present disclosure.

The third aspect of the present disclosure relates to a cocrystal of pterostilbene and a coformer as defined above for use as a medicament. It is also disclosed crystalline Form VI of pteroltilbene as defined above for use as a medicament.

Particularly, the cocrystal of pterostilbene and a coformer, or the crystalline Form VI of pterostilbene as defined above, are for use in the prophylaxis and/or treatment of neurological, cardiovascular, metabolic, hematologic disorders, cancer, atherosclerosis, diabetes mellitus, inflammation, dyslipidemia, osteoporosis and other age-related diseases not previously mentioned.

This aspect could be also formulated as the use of the a cocrystals of pterostilbene and a coformer as defined above for the preparation of a medicament for the prophylaxis and/or treatment of neurological, cardiovascular, metabolic, and hematologic disorders, cancer, atherosclerosis, diabetes mellitus, inflammation, dyslipidemia, osteoporosis and other age-related diseases not previously mentioned. It also relates to a method for the prophylaxis and/or treatment of a mammal suffering, or susceptible to suffer, from a neurological, cardiovascular, metabolic, or hematologic disorder, cancer, atherosclerosis, diabetes mellitus, inflammation, dyslipidemia, osteoporosis and other age-related diseases not previously mentioned wherein the method comprises administering to said mammal an effective amount of the cocrystal of pterostilbene and a coformer, or the crystalline Form VI of pteroltilbene, as defined above together with one or more acceptable excipients or carriers.

Throughout the description and claims the word "comprise" and variations of the word, are not intended to exclude other technical features, additives, components, or steps.

Furthermore, the word "comprise" encompasses the case of "consisting of". Additional objects, advantages and features of the present disclosure will become apparent to those skilled in the art upon examination of the description or may be learned by practice of the present disclosure. The following examples and drawings are provided by way of illustration, and they are not intended to be limiting of the present disclosure. Furthermore, the present disclosure covers all possible combinations of particular and preferred embodiments described herein.

EXAMPLES

General Considerations

Pterostilbene, picolinic acid, 1,4-dimethylpiperazine, 2,3,5-trimethylpirazine, theophylline, 1,4,8,11-tetrazacyclohexandecane, ethylendiamine, 1,4-diazabicyclo[2.2.2]octane (DABCO), are commercially available.

Powder X-Ray diffraction (PXRD) analyses were performed by sandwiching the powder samples between polyester films of 3.6 microns of thickness analysed in a PANalytical X'Pert PRO MPD θ/θ powder diffractometer of 240 millimetres of radius, in a configuration of convergent beam with a focalizing mirror and a flat sample transmission geometry, in the following experimental conditions: Cu Kα radiation (λ=1.5418 Å); Work power: 45 kV and 40 mA; Incident beam slits defining a beam height of 0.4 millimetres; Incident and diffracted beam 0.02 radians Soller slits; PIXcel detector: Active length=3.347°; 2θ/θ scans from 2 to 40° 2θ with a step size of 0.026° 2θ and a measuring time of 76 seconds per step.

Example 1.—Preparation of a Cocrystal of Pterostilbene:Picolinic Acid (1:1)

Pterostilbene (200 mg, 0.780 mmol) and picolinic acid (24 mg, 0.195 mmol) were mixed and stirred in toluene (0.8 mL) overnight at room temperature. The resulting suspension was filtered and dried under vacuum.

Example 2.—Preparation of a Cocrystal of Pterostilbene:Picolinic Acid (2:1)

A saturated solution of pterostilbene (5000 mg) in toluene (23.6 mL) was prepared at 60° C. Then, the solution was cooled down at 25° C. and picolinic acid (1635 mg) was added. The suspension was stirred during 2 hours at 25° C. and it was filtered and dried under vacuum.

Example 3.—Preparation of a Cocrystal of Pterostilbene: 1,4-Dimethylpiperazine (2:1)

Pterostilbene (97.6 mg, 0.381 mmol) and 1,4-dimethylpiperazine (0.3 mL) were mixed and stirred overnight at room temperature. The resulting suspension was filtered and dried under vacuum.

Example 4.—Preparation of a Cocrystal of Pterostilbene: 2,3,5-Trimethylpirazine (2:1)

Pterostilbene (61.3 mg, 0.239 mmol) and 2,3,5-trimethylpirazine (0.05 mL) were mixed and stirred overnight at room temperature. The resulting suspension was filtered and dried under vacuum.

Example 5.—Preparation of a Cocrystal of Pterostilbene:Theophylline (1:1)

Pterostilbene (113 mg, 0.441 mmol) was dissolved in dichloromethane (0.2 mL) at room temperature. Then, theophylline (20 mg, 0.111 mmol) was added and the resulting suspension was stirred overnight and it was filtered and dried under vacuum. Then, the solid was placed into a round-bottomed flask and it was heated up to 80° C. in a silicone oil bath under vacuum for 1 hour, until total desolvation.

Example 6.—Preparation of a Cocrystal Solvate of Pterostilbene:Theophylline:Dichloromethane (1:1:1)

Pterostilbene (113 mg, 0.441 mmol) was dissolved in dichloromethane (0.2 mL) at room temperature. Then, theophylline (20 mg, 0.111 mmol) was added and the resulting suspension was stirred overnight and it was filtered and dried under vacuum.

Example 7.—Preparation of a Cocrystal of Pterostilbene: 1,4,8,11-Tetrazacyclohexandecane Cocrystal (2:1)

Pterostilbene (50 mg, 0.195 mmol) and 1,4,8,11-tetrazacyclohexandecane (20 mg, 0.0998 mmol) were mixed and dissolved in chloroform (0.3 mL) at room temperature. Then, the solution was kept sealed at room temperature. After 35 days, the obtained crystals were filtered and dried under vacuum.

Example 8.—Preparation of a Pterostilbene:Ethylendiamine Cocrystal (2:1)

Pterostilbene (50 mg, 0.195 mmol) was dissolved in ethylendiamine (0.05 mL) at 50° C. Then, the mixture was cooled down at room temperature slowly and it was kept sealed at room temperature. After 5 days, the mixture crystallized and it was filtered and dried under vacuum.

Example 9.—Preparation of a Pterostilbene:Ethylendiamine:$H_2O$ Cocrystal Hydrate (2:1:2)

Pterostilbene (162 mg, 0.632 mmol) and ethylendiamine (2 mL) were mixed and stirred overnight at room temperature. The resulting suspension was filtered and dried under vacuum.

Example 10.—Preparation of a Pterostilbene:DABCO Cocrystal (2:1)

DABCO (100.0 mg, 0.892 mmol) was dissolved in xylene (1.5 mL) at 50° C. Then, the solution was cooled down at room temperature slowly and pterostilbene (197.1 mg, 0.769 mmol) was added and the mixture was stirred overnight. The resulting suspension was filtered and dried under vacuum.

Example 11.—Preparation of a Pterostilbene: 2,4-Dihydroxybenzoic Acid Cocrystal A saturated solution of pterostilbene (100 mg) in IPA (0.25 mL) was prepared at 25° C. Then, 2,4-dihydroxybenzoic acid (131.7 mg) was added and it was stirred overnight at 25° C. The resulting suspension was filtered and dried under vacuum.

Example 12.—Preparation of a Pterostilbene:Indole Cocrystal

Pterostilbene (20 mg, 0.0780 mmol) and indole (9.2 mg, 0.078 mmol) were grinded in benzyl alcohol during 15 minutes at 25° C.

Example 13.—Preparation of a Pterostilbene:Lysine Cocrystal

A saturated solution of pterostilbene (50 mg) in ACN (0.1 mL) was prepared at 25° C. Then, lysine (34.9 mg) was added and it was stirred overnight at 25° C. The resulting suspension was filtered and dried under vacuum.

Example 14.—Preparation of a Pterostilbene:Orotic Acid Cocrystal

Pterostilbene (20 mg, 0.0780 mmol) and orotic acid (12.2 mg, 0.078 mmol) were grinded in DMSO during 15 minutes at 25° C.

Example 15.—Preparation of a Pterostilbene: 1,10-Phenanthroline Cocrystal [1:1]

A saturated solution of pterostilbene (100 mg) in MEK (0.2 mL) was prepared at 25° C. Then, 1,10-phenanthroline (70.3 mg) was added and the suspension was stirred overnight at 25° C. The resulting suspension was filtered and dried under vacuum.

Example 16.—Preparation of a Pterostilbene:Urea Cocrystal

Pterostilbene (20 mg, 0.0780 mmol) and urea (4.7 mg, 0.078 mmol) were grinded in benzyl alcohol during 15 minutes at 25° C.

Example 17.—Preparation of Form VI of Pterostilbene

Pterostilbene (20 mg, 0.0780 mmol) and acetone (1 drop) were grinded at a vibration frequency of 30 Hz for 15 minutes at room temperature, resulting in form VI.

Example 18.—Disolution Rate of Pterostilbene Vs Cocrystals

1. Molar Extinction Coefficient (MEC) Determination in FaSSIF v2 Medium

Molar extinction coefficients of pterostilbene and of each coformer were determined by UV-metric titration using a GIpKa™ titrator (Sirius Analytical Instruments, UK). Briefly, a 10 mM stock solution of sample was prepared in DMSO. 50 μL of sample stock solution and 0.25 mL of a 15 mM potassium phosphate buffer were added to 10 mL of a 0.15 M KCl solution, which in turn contained 17.9 mg of FaSSIF v2 powder. The pH of the sample solution was adjusted to 2 with 0.5 M HCl before starting the titration, and then the titration was done using 0.5 M KOH up to pH 12. The UV absorption spectra (between 250 and 450 nm) of the solution were recorded at each titrant addition by a fiber optic dip-probe. The collected data were refined through the RefinamentPro software, and the pKa values and Molar Extinction Coefficients obtained by Target Factor Analysis.

2. Dissolution Rate Experiments

Tablet production: tablets of 3 mm diameter were prepared using a manual hydraulic tablet press (Applied Measurements Ltd, UK). The applied pressure was 100 Kg for 2 min. From 10 to 15 mg of each solid form, pterostilbene or cocrystal, were weighted. The total exposed surface area was 0.5 $cm^2$.

Medium: FaSSIF v2 (pH 6.5), with corresponding amount of phosphoric (28.4 mM) acid instead of maleic acid.

Dissolution tests were performed with a small-scale dissolution assay installed in a GIpKa™ titrator (Sirius Analytical Instruments, UK).

Dissolution time and temperature: 120 minutes and 25° C.

Procedure: 15 mL of FaSSIF v2 was added into the sample vial containing the tablet. Spectra collection started immediately after. Spectra were recorded every 30 seconds between 250 and 450 nm through a Sirius D-PAS spectrometer with a bifurcated optic fibre dip probe (Hellma Analytics). The medium was stirred at a constant rate.

3. UV-Vis Quantification

The concentration of pterostilbene in solution at each time point is determined from the spectroscopic data by applying the Beer-Lambert law, using previously determined molar extinction coefficients of pure pterostilbene. Spectrum regions where signal is saturated (A>1.5) or presenting medium interferences were discarded. Then, the concentration data were converted into absolute sample quantities, and used to generate the graphs showing the sample quantity vs. time.

4. Determination of the Dissolution Rate

Dissolution rate is obtained through the fit of the first order Noyes-Whitney exponential equation to the data:

$$[X]_t = S(1-e-k_d(t-t_0))$$

In this equation, $[X]_t$ is the weight in grams of compound in solution at the experiment time (min); S is the extrapolated solubility (g) of pterostilbene; $k_d$ is the rate constant for dissolution ($min^{-1}$); and $t_0$ (min) is a term allowing for a temporal offset. Results are calculated using a refinement process in which S, $k_d$ and $t_0$ are varied in order to minimize the root mean square deviation between the modelled concentrations and the measured concentrations. The dissolution rate (g $min^{-1}$) is given by the product $k_dS$ (T. Gravestock et al., 2011). Results are shown in Table 18.

TABLE 18

| Solid form | dissolution rate (nmol/min) |
|---|---|
| Pterostilbene | 13.2 ± 2.1 |
| Pterostilbene (Form VI) | 7.4 ± 1.8 |
| Pterostilbene:picolinic acid cocrystal (1:1) | 427.8 ± 29.5 |
| Pterostilbene:ethylendiamine cocrystal | 176.1 ± 12.6 |
| Pterostilbene:ethylendiamine hydrate cocrystal | 230.4 ± 26.59 |
| Pterostilbene:theophylline cocrystal | 33.5 ± 6.7 |
| Pterostilbene:2,3,5-trimethylpirazine cocrystal | 52.0 ± 5.8 |
| Pterostilbene:caffeine cocrystal | 45.4 ± 9.2 |
| Pterostilbene:picolinic acid cocrystal (2:1) | 351.3 ± 18.9 |

Figure 16:
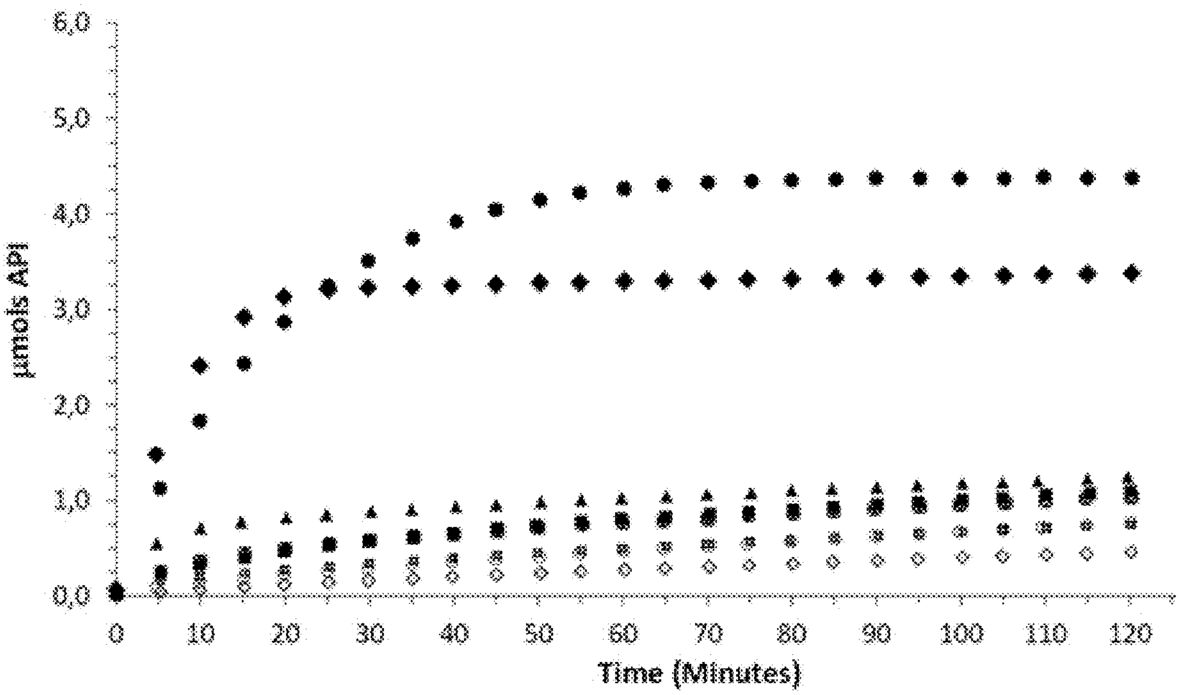
FIG. 16 shows the dissolution profiles of pterostilbene cocrystals compared to pterostilbene Form I and pterostilbene Form VI, were.

The comparison between dissolution rate curves of the solid forms listed in Table 18 is shown in FIG. 16 and FIG. 17.

Example 19.—Pharmacokinetics of Pterostilbene Vs Cocrystal of Pterostilbene and Picolinic Acid In-Life Phase Animals: Male Sprague-Dawley rats (weight: 417.9-458.6 g)

Administration: Oral (single dose)

Dose: 20 mg/kg P56 (pterostilbene, free base)

20 mg/kg P56-VIII (cocrystal of pterostilbene and picolinic acid;

13.5 mg/kg as pterostilbene free base)

Formulation: Suspension (0.5% carboxymethylceluulose, CMC)

Adm. volume: 10 ml/kg

Fed/fasted state: Fasted (at least 8 hours prior dosing)

Sampling: Six blood samples/animal (1, 2, 4, 6, 8 and 24 hours post-adm.)

Plasma samples: Plasma samples using $K_3$-EDTA as anticoagulant.

Samples were immediately frozen at −80° C. until their analysis

Pharmacokinetic analysis was performed by non-compartmental pharmacokinetic analysis using Kinetica v5 software (Alfasoft Limited, Luton, UK). Descriptive statistics was performed using Microsoft Excel spreadsheet 2007 (Microsoft Inc, Redmond, US). Plasma bioanalysis was made by LC-MS/MS.

Concentration values below the lower limit of quantification (BLQ) were set to zero, whereas missing concentration values were not considered for statistical and pharmacokinetic evaluations. All computations used the nominal sampling times, nominal doses and concentrations levels were expressed as free base. The numerical data presented below were computer generated. Because of rounding, recalculation of derived values from individual data presented herein below could, in some instances, yield minor variation.

The area under the plasma concentration-time curve from 0 to t ($AUC_{0-t}$) was determined by using the trapezoidal rule. For i.v. bolus studies, the extrapolated AUC from time 0 to first data point did not exceed 20%. The terminal half-life was determined according to the following rules: (a) time interval equal to at least $1.5 \times t_{1/2}$, (b) regression analysis (straight line on the log-transformed scale) contained data from at least 3 different time points in the terminal phase and as many data points as possible (always including the last quantifiable concentration but excluding the $C_{max}$), and (c) the coefficient of determination ($r^2$) was ≥0.85. If at least one of these three conditions was not fulfilled, the terminal half-life and the parameters depending on $t_{1/2}$ were listed but flagged as not reliably calculated. If the percentage of extrapolated AUC was more than 20%, the individual $AUC_{inf}$ result were listed but flagged as not reliably calculated. Flagged parameters were not included in descriptive statistics and statistical testing procedures.

Pharmacokinetics of P56 in rat plasma after single oral administration is shown in Tables 19 and 20 below (FIG. 18):

TABLE 19

Plasma levels of pterostilbene in rats after single oral administration (20 mg/kg P56).

| Time (h) | Concentration (ng/ml) 1 | 2 | 3 | 4 | 5 | Mean* (ng/ml) | SD | CV (%) |
|---|---|---|---|---|---|---|---|---|
| Pre-dose | BLQ | BLQ | BLQ | BLQ | BLQ | BLQ | — | — |
| 1 | 131.6 | 87.3 | 94.5 | 93.0 | 80.6 | 97.4 | 19.9 | 20.4 |
| 2 | 164.9 | 91.8 | 116.0 | 166.9 | 84.5 | 124.9 | 39.3 | 31.5 |
| 4 | BLQ | 68.3 | 65.4 | 96.1 | 49.9 | 55.9 | 35.4 | 63.3 |
| 6 | BLQ | 54.7 | 26.9 | 68.2 | 40.4 | 38.1 | 26.3 | 69.1 |
| 8 | BLQ | BLQ | 11.2 | 32.5 | 15.1 | 11.8 | 13.4 | 114 |
| 24 | BLQ | BLQ | BLQ | 6.51 | BLQ | BLQ | 2.9 | — |

*Arithmetic mean
BLQ values (<5 ng/ml)

TABLE 20

Plasma pharmacokinetic parameters of pterostilbene in rats after single oral adm. (20 mg/kg P56).

| An | $C_{max}$ (ng/ml) | $t_{max}$* (h) | $t_{1/2}$ (h) | $n_{points}$ ($r^2$) | $AUC_{0-t}$ (ng · h/ml) | $AUC_{inf}$ (ng · h/ml) |
|---|---|---|---|---|---|---|
| 1 | 164.9 | 2 | NC | — | 214 | NC |
| 2 | 91.8 | 2 | 5.4 | 3 (0.993) | 416 | 839 |
| 3 | 116.0 | 2 | 1.6 | 3 (0.999) | 464 | 490 |
| 4 | 166.9 | 2 | 5.4 | 4 (0.955) | 1017 | 1067 |
| 5 | 84.5 | 2 | 2.3 | 3 (0.878) | 403 | 454 |
| Mean | 124.8 | 2 | 3.7 | 3 | 575 | 712 |
| SD | 39.3 | (2-2) | 2.0 | (>0.850) | 295 | 294 |
| CV % | 31.5 | | 54.8 | | 51.4 | 41.2 |

NC: not quantifiable
*Median (min-max)
$C_{max}$: maximum observed concentration
$t_{max}$: time of occurrence of $C_{max}$
$t_{1/2}$: terminal elimination half-life or apparent terminal elimination half-life
$AUC_{inf}$: Area Under the Curve from 0 to infinity
$AUC_{0-t}$: Area Under the Curve from 0 to the time of the last quantifiable concentration Pharmacokinetics of P56-VIII in rat plasma after single oral administration is shown in Tables 21 and 22 (FIG. 19).

TABLE 21

Plasma levels of pterostilbene in rats after single oral administration (20 mg/kg P56-VIII).

| Time (h) | Concentration (ng/ml) 1 | 2 | 3 | 4 | 5 | Mean* (ng/ml) | SD | CV (%) |
|---|---|---|---|---|---|---|---|---|
| Pre-dose | BLQ | BLQ | BLQ | BLQ | BLQ | 0.0 | — | — |
| 1 | 513.3 | 980.0 | 189.8 | 695.2 | 145.5 | 504.7 | 350.2 | 69.4 |
| 2 | 462.8 | 952.8 | 301.1 | 587.9 | 266.9 | 514.3 | 277.0 | 53.9 |
| 4 | 262.6 | 991.8 | 224.7 | 538.5 | 240.8 | 451.7 | 328.3 | 72.7 |
| 6 | 150.6 | 663.7 | 153.8 | 222.5 | 337.4 | 305.6 | 214.0 | 70.0 |
| 8 | 210.5 | 449.2 | 53.5 | 136.4 | 224.6 | 214.8 | 147.7 | 68.7 |
| 24 | 16.4 | 7.67 | BLQ | 7.16 | 6.50 | 7.54 | 5.83 | 46.9 |

*Arithmetic mean
BLQ values (<5 ng/ml)

TABLE 22

Plasma pharmacokinetic parameters of pterostilbene in rats after single oral adm. ((20 mg/kg P56-VIII, 13.5 mg as pterostilbene).

| An | $C_{max}$ (ng/ml) | $t_{max}$* (h) | $t_{1/2}$ (h) | $n_{points}$ ($r^2$) | $AUC_{0-t}$ (ng · h/ml) | $AUC_{inf}$ (ng · h/ml) | $f_{rel}$ |
|---|---|---|---|---|---|---|---|
| 1 | 513.3 | 1 | 5.1 | 4 (0.961) | 4059 | 4178 | — |
| 2 | 991.8 | 4 | 2.8 | 3 (0.999) | 9824 | 9855 | — |
| 3 | 301.1 | 2 | 1.9 | 3 (0.931) | 1452 | 1602 | — |
| 4 | 695.2 | 1 | 3.7 | 3 (0.999) | 4384 | 4422 | — |
| 5 | 337.4 | 6 | 3.2 | 3 (0.999) | 3776 | 3805 | — |
| Mean | 567.8 | 2 | 3.3 | 3 | 4699 | 4772 | 9.91 |
| SD | 284.2 | (1-6) | 1.2 | (>0.850) | 3089 | 3054 | — |
| CV % | 50.1 | | 35.1 | | 65.7 | 64.0 | — |

*Median (min-max)
Relative f calculated as $f_{rel}$ = ($AUC_{inf}$ P56-VIII/Dose)/($AUC_{inf}$ FI/Dose), doses expressed as pterostilbene (free base).

Comparison of plasma concentration-time profiles of pterostilbene in rats after single oral administration of P56 (20 mg/kg pterostilbene) and P56-VIII (13.5 mg/kg pterostilbene) is shown in FIG. 20.

Following single oral administration of 20 mg/kg P56 (pterostilbene, free base) to male SD rats, plasma $C_{max}$ was attained at 2 hours after dosing. The mean $C_{max}$ value was 124.8 ng/ml and plasma levels were detected until 8 hours post-dosing in 4 out of 5 animals at a concentration level close to the limit of quantification (5 ng/ml). The terminal half-life of pterostilbene was estimated as 3.7 hours, whereas the variability of $C_{max}$ and $AUC_{inf}$ was of 31.5% and 41.2%, respectively.

After the single oral dose administration of 20 mg/kg of the pterostilbene-picolinic acid cocrystal (13.5 mg/kg as pterostilbene), a higher variability in the oral absorption was observed compared to the P56 formulation, with a $t_{max}$ value ranging from 1 to 6 hours post-dosing. The terminal half-life was 3.3 hours, which is comparable to that found for the P56 formulation. Compared to the previous formulation, there was an important increase in the $C_{max}$ and $AUC_{inf}$ values, which accounted for around 6- and about 10-fold, respectively. These results confirm that the systemic bioavailability with picolinic acid is substantially increased for pterostilbene as a picolinic acid cocrystal, with a relative bioavailability ($f_{rel}$) of 9.9. But, an increase around 20% in the variability of pterostilbene $C_{max}$ and $AUC_{inf}$ values was observed for the cocrystal formulation.

The results obtained in this study are comparable to that found in the literature after oral administration. Although, it is worth to remark that a reduced systemic clearance of pterostilbene was observed when oral dosing is increased above of 25 mg/kg and an increased oral bioavailability is found in fed state.

CITATION LIST

T. Gravestock et al., "The "GI dissolution" method: a low volume, in vitro apparatus for assessing the dissolution/precipitation behaviour of an active pharmaceutical ingredient under biorelevant conditions" *Anal. Methods,* 2011, vol. 3, pp. 560-567.

The invention claimed is:

1. A cocrystal of pterostilbene and picolinic acid, wherein the cocrystal is characterized by having an X-ray powder diffractogram that comprises characteristic peaks at 5.6, 13.5, 14.0, 21.8 and 24.4±0.3 degrees 2 theta (Cu-$K_\alpha$ radiation, λ=1.5418 Å).

2. A composition comprising an effective amount of the cocrystal of pterostilbene and picolinic acid as defined in claim 1 together with one or more appropriate acceptable excipients or carriers.

3. The composition according to claim 2, wherein the composition is a pharmaceutical composition further comprising one or more active ingredients selected from the group consisting of antiinflamatory agents, chemotherapeutic agents, immunomodulatory agents, cancer hormone therapeutic agents, targeted cancer therapeutic agents, antidiabetic agents, lipid lowering agents, antiarthritic agents, dementia treatment agents, antiatherosclerotic agents, antiobesity agents, and antiosteoporotic agents.

4. The composition according to claim 2, wherein the composition is a dietary supplement further comprising one or more active ingredients selected from the group consisting of L-carnitine, xylitol, vitamins, carotenoids, omega-3 fatty acids, flavonoids, coenzime Q10, natural products inhibiting 5-LOX, harpagoside, copper, zinc, and manganese.

5. The cocrystal of pterostilbene and picolinic acid according to claim 1, wherein the molar ratio of pterostilbene to picolinic acid is 1:1.

6. A cocrystal of pterostilbene and picolinic acid, wherein the cocrystal is characterized by having an X-ray powder diffractogram that comprises characteristic peaks at 3.2, 16.8, 18.3, 23.6 and 26.0±0.3 degrees 2 theta (Cu-$K_\alpha$ radiation, λ=1.5418 Å).

7. The cocrystal of pterostilbene and picolinic acid according to claim 6, wherein the molar ratio of pterostilbene to picolinic acid is 2:1.

8. A composition comprising an effective amount of the cocrystal of pterostilbene and picolinic acid of claim 6 together with one or more appropriate acceptable excipients or carriers.

9. The composition according to claim 8, wherein the composition is a pharmaceutical composition further comprising one or more active ingredients selected from the group consisting of antiinflamatory agents, chemotherapeutic agents, immunomodulatory agents, cancer hormone therapeutic agents, targeted cancer therapeutic agents, antidiabetic agents, lipid lowering agents, antiarthritic agents, dementia treatment agents, antiatherosclerotic agents, antiobesity agents, and antiosteoporotic agents.

10. The composition according to claim 8, wherein the composition is a dietary supplement further comprising one or more active ingredients selected from the group consisting of L-carnitine, xylitol, vitamins, carotenoids, omega-3 fatty acids, flavonoids, coenzime Q10, natural products inhibiting 5-LOX, harpagoside, copper, zinc, and manganese.

* * * * *